US009689089B2

(12) United States Patent
Ishikawa et al.

(10) Patent No.: US 9,689,089 B2
(45) Date of Patent: Jun. 27, 2017

(54) SOLUTION-DYED PROTEIN FIBER AND METHOD FOR PRODUCING SAME

(71) Applicant: SPIBER INC., Tsuruoka-shi, Yamagata (JP)

(72) Inventors: Mizuki Ishikawa, Tsuruoka (JP); Kazuhide Sekiyama, Tsuruoka (JP)

(73) Assignee: SPIBER INC., Yamagata (JP)

( * ) Notice: Subject to any disclaimer, the term of this patent is extended or adjusted under 35 U.S.C. 154(b) by 0 days.

(21) Appl. No.: 14/405,101

(22) PCT Filed: Apr. 26, 2013

(86) PCT No.: PCT/JP2013/062429
§ 371 (c)(1),
(2) Date: Dec. 2, 2014

(87) PCT Pub. No.: WO2014/002605
PCT Pub. Date: Jan. 3, 2014

(65) Prior Publication Data
US 2015/0141618 A1 May 21, 2015

(30) Foreign Application Priority Data
Jun. 28, 2012 (JP) ................................. 2012-145225

(51) Int. Cl.
| D01F 4/02 | (2006.01) |
| D01F 4/00 | (2006.01) |
| D01F 1/06 | (2006.01) |
| C07K 14/43 | (2006.01) |
| D01D 5/04 | (2006.01) |
| D01D 5/06 | (2006.01) |
| C07K 14/435 | (2006.01) |
| D01D 1/02 | (2006.01) |

(52) U.S. Cl.
CPC .......... *D01F 4/02* (2013.01); *C07K 14/43518* (2013.01); *D01D 1/02* (2013.01); *D01D 5/04* (2013.01); *D01D 5/06* (2013.01); *D01F 1/06* (2013.01); *D01F 4/00* (2013.01)

(58) Field of Classification Search
None
See application file for complete search history.

(56) References Cited

U.S. PATENT DOCUMENTS

| 5,171,505 A | 12/1992 | Lock |
| 5,252,285 A | 10/1993 | Lock |
| 6,620,917 B1 | 9/2003 | Mello et al. |
| 7,057,023 B2 | 6/2006 | Islam et al. |
| 8,278,416 B1 | 10/2012 | Johansson et al. |
| 2003/0155670 A1 | 8/2003 | O'Brien |
| 2004/0102614 A1 | 5/2004 | Islam et al. |
| 2004/0132957 A1 | 7/2004 | Asakura |
| 2005/0054830 A1 | 3/2005 | Islam et al. |
| 2005/0158821 A1 | 7/2005 | Mello et al. |
| 2009/0226969 A1 | 9/2009 | Johansson et al. |
| 2009/0318963 A1 | 12/2009 | Asakura |
| 2012/0329992 A1 | 12/2012 | Johansson et al. |
| 2013/0172478 A1 | 7/2013 | Bausch |
| 2014/0058066 A1 | 2/2014 | Sekiyama et al. |
| 2014/0245923 A1 | 9/2014 | Sugahara et al. |

FOREIGN PATENT DOCUMENTS

| CN | 1078509 | 11/1993 |
| CN | 1952225 | 4/2007 |
| CN | 101705559 | 5/2010 |
| CN | 101724920 | 6/2010 |
| EP | 0559725 | 9/1993 |
| EP | 0816505 | 1/1998 |
| JP | 4-263614 | 9/1992 |
| JP | 5-263312 | 10/1993 |
| JP | 6-502993 | 4/1994 |
| JP | 8-74123 | 3/1996 |
| JP | 2004-503204 | 2/2004 |
| JP | 2005-515309 | 5/2005 |

(Continued)

OTHER PUBLICATIONS

Tsukada et al., "Structural Changes and Dyeability of Silk Fibroin Fiber Following Shrinkage in Neutral Salt Solution", J. Appl. Polymer Sci., 1994, 51(4), pp. 619-624.*

Phipps et al., "Analysis of Azo Dyes Using a Core Enhanced Technology Accucore HPLC Column", Thremo Scientific, Aug. 2011, pp. 1-2. Retrieved from < https://tools.thermofisher.com/content/sfs/brochures/ANCCSCETAZODYE_0611.pdf > on Oct. 27, 2016.*

López-Cortés et al., "Screening and Isolation of PHB-Producing Bacteria in a Polluted Marine Microbial Mat", Microb Ecol (2008) 56:112-120. DOI 10.1007/s00248-007-9329-8.*

Davies et al., (2003) "Measurement of Isoketal Protein Adducts by Liquid Chromatography-Electrospray Ionization/Tandem Mass Spectrometry", in Hensley & Ford (Eds.), Methods in Biological Oxidate Stress (Chapter 15, p. 30). Totowa, New Jersey:Humana Press.*

(Continued)

*Primary Examiner* — Suzanne M Noakes
(74) *Attorney, Agent, or Firm* — Hamre, Schumann, Mueller & Larson, P.C.

(57) ABSTRACT

A solution-dyed protein fiber of the present invention includes 0-100 mass % of silk fibroin and 100-0 mass % of a polypeptide derived from spider silk proteins when the protein fiber is assumed to be 100 mass %, wherein the solution-dyed protein fiber contains a solution-dyeing colorant. The fiber is obtained by: dissolving or dispersing a solution-dyeing colorant in a solvent used for a spinning solution or in dimethyl sulfoxide, thereby preparing a coloring liquid; adding a solvent to the coloring liquid in an amount necessary for a spinning solution; adding and dissolving protein powder into the solvent, thereby preparing a spinning solution; and subjecting the spinning solution to wet spinning or dry-wet spinning. Thereby, the present invention provides a low-cost solution-dyed protein fiber in which a solution-dyeing colorant is dispersed uniformly and that can exhibit bright color tone, and a method for producing the same.

15 Claims, 4 Drawing Sheets

(56) References Cited

FOREIGN PATENT DOCUMENTS

| JP | 2007-303015 | 11/2007 |
|---|---|---|
| JP | 2009-521921 | 6/2009 |
| JP | 2010-024586 | 2/2010 |
| JP | 4945768 B | 6/2012 |
| JP | 2012-136795 | 7/2012 |
| WO | WO 92/09695 | 6/1992 |
| WO | WO 01/36531 | 5/2001 |
| WO | WO 01/70973 | 9/2001 |
| WO | WO 2008/004356 | 1/2008 |
| WO | WO 2012/123450 | 10/2010 |
| WO | WO 2011/113592 | 9/2011 |
| WO | WO 2012/165477 | 12/2012 |
| WO | WO 2013/065650 | 5/2013 |
| WO | WO 2013/065651 | 5/2013 |

OTHER PUBLICATIONS

Elices et al.: "Bioinspired Fibers Follow the Track of Natural Spider Silk"; Macromolecules (2011), 44, pp. 1166-1176.

Guerette et al.: "Silk Properties Determined by Gland-Specific Expression of a Spider Fibroin Gene Family"; Science (1996), vol. 727, pp. 112-115.

Xia et al.: "Native-sized recombinant spider silk protein produced in metabolically engineered *Escherichia coli* results in a strong fiber"; Proc. Natl. Acad.Sci. (PNAS) (2010), vol. 107, No. 32, pp. 14059-14063.

Lazaris et al.: "Spider Silk Fibers Spun from Soluble Recombinant Silk Produced in Mammalian Cells"; Science 295, pp. 472-476, Jan. 18, 2011.

Xia et al.: "Native-sized recombinant spider silk protein produced in metabolically engineered *Escherichia Coli* results in a strong fiber"; PNAS vol. 107, No. 32, pp. 14059-14063, Aug. 10, 2010.

Elices et al.: "Bioinspired Fibers Follow the Track of Natural Spider Silk"; Macromolecules, vol. 44, No. 5, pp. 1166-1176, Apr. 2, 2011.

Agnarsson et al.: "Bioprospecting Finds the Toughest Biological Material: Extraordinary Silk from a Giant Riverine Orb Spider"; PLOS ONE, vol. 5, Issue 9, Sep. 2010.

Heim et al.: "Spider Silk: From Soluble Protein to Extraordinary Fiber"; Angewandte Chemie International Edition, vol. 48, No. 20. May 2009, pp. 3584-3596.

Extended European Search Report, Feb. 9, 2015; European Application No. 12793074.1 (9 pages).

Office Action issued in corresponding Chinese Application No. 201380034158.4, Jul. 27, 2015, 7 pages.

Office Action issued in corresponding Chinese Patent Application No. 201380034158.4, Feb. 29, 2016, 12 page with a partial English translation.

Extended European Search Report issued in corresponding European Application No. 13810001.1, Dec. 18, 2015, 7 pages.

\* cited by examiner

US 9,689,089 B2

SOLUTION-DYED PROTEIN FIBER AND METHOD FOR PRODUCING SAME

TECHNICAL FIELD

The present invention relates to a solution-dyed protein fiber to which a solution-dyeing colorant has been added before a spinning process, and a method for producing the same.

BACKGROUND ART

As protein fibers, fibroin fibers that are regenerated silk fibers, artificial spider silk fibers, and the like are known. Some solution-dyed fibers of these protein fibers have already been proposed. For example, Patent Document 1 proposes a method for producing a regenerated silk fiber, including; adding silk fibroin and hematin into a hexafluoroisopropanol (HFIP) solvent; extruding the solution into a methanol coagulation liquid for spinning; and performing cold drawing. As the artificial spider silk fibers, for example, Patent Document 2 describes addition of Sudan red or Nile red (both of them are pigments) into a spinning solution in Example 6, and addition of Green Fluorescent Protein (GFP) into a spinning solution in Example 7.

However, there are problems with the dispersibility of such pigments into a spinning solution and the cost of GFP. Poor dispersibility or solubility of pigments into a spinning solution will result not only in yarn breakage in a spinning process but also difficulty in obtaining solution-dyed fibers with uniform composition. Additionally, bright colors are less likely to be exhibited.

PRIOR ART DOCUMENTS

Patent Documents

Patent Document 1; WO 2008/004356
Patent Document 2; WO 2011/113592

DISCLOSURE OF INVENTION

Problem to be Solved by the Invention

In order to solve the above conventional problems, the present invention provides a low-cost solution-dyed protein fiber in which a solution-dyeing colorant is dispersed uniformly and that can exhibit bright color tone, and a method for producing the same.

Means for Solving Problem

A solution-dyed protein fiber of the present invention is a solution-dyed protein fiber including 0-100 mass % of silk fibroin and 100-0 mass % of a polypeptide derived from spider silk proteins when the protein fiber is assumed to be 100 mass %. The solution-dyed protein fiber contains a solution-dyeing colorant.

A method for producing a solution-dyed protein fiber of the present invention is a method for producing a solution-dyed protein fiber including 0-100 mass % of silk fibroin and 100-0 mass % of a polypeptide derived from spider silk proteins when the protein fiber is assumed to be 100 mass %, the method including; dissolving or dispersing a solution-dyeing colorant in a solvent used for a spinning solution or in dimethyl sulfoxide, thereby preparing a coloring liquid; adding a solvent to the coloring liquid in an amount necessary for a spinning solution; adding and dissolving protein powder into the solvent, thereby preparing a spinning solution; and subjecting the spinning solution to wet spinning or dry-wet spinning.

Effect of the Invention

In the present invention, by configuring a solution-dyed protein fiber by adding a solution-dyeing colorant to a spinning solution, it is possible to provide a low-cost solution-dyed protein fiber in which a solution-dyeing colorant is dispersed uniformly and that can exhibit a bright color tone, and a method for producing the same. Depending on the mixing ratio of the silk fibroin and the polypeptide derived from spider silk proteins, it is possible to obtain a fiber having reflectivity that is bright enough to exhibit metallic luster.

BRIEF DESCRIPTION OF DRAWINGS

FIG. 2A shows a spinning process,
and FIG. 2B shows a drawing process.

Figure 1:
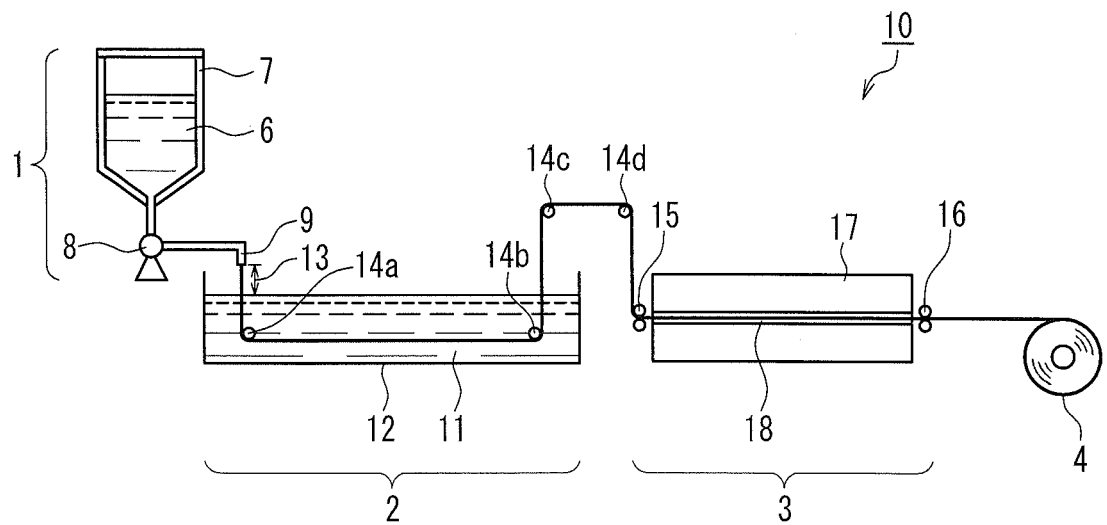
FIG. 1 is an explanatory view showing a production process in one example of the present invention

DESCRIPTION OF THE INVENTION (1) Solution-Dyeing Colorant
The fiber of the present invention is a solution-dyed protein fiber obtained by adding a solution-dyeing colorant (hereinafter, also referred to as a colorant) into a spinning solution and subjecting the solution to spinning. The colorant is preferably at least one selected from dyes and pigments. There are dyes that can exhibit various color tones and can be dissolved or dispersed into a spinning solution easily. In the present invention, the temperature of a spinning process is not so high as to degrade dyes, so that a variety of dyes can be used. Further, pigments have an advantage of high weather resistance. A further preferable colorant is at least one selected from a fiber acid dye, a fiber basic dye, a fiber fluorescent dye, a fiber direct dye, a fiber disperse dye, a plant pigment, a food natural pigment, and a carbon black. These colorants have favorable dispersibility with respect to a spinning solution, and they are less likely to generate foreign substances. Among these, the acid dye and the plant pigment have favorable affinity for all of the following: silk fibroin alone, a polypeptide derived from spider silk proteins alone, and a mixed composition of the silk fibroin and the polypeptide derived from spider silk proteins, and exhibit bright color tone. Depending on the mixing ratio of the silk fibroin and the polypeptide derived from spider silk proteins, it is possible to obtain a fiber having reflectivity that is bright enough to exhibit metallic luster. The fluorescent dye is useful for a solution-dyed fiber of the polypeptide derived from spider silk proteins alone, and exhibits a strong fluorescent color. The abundance of the colorant is preferably 0.1 to 2 mass % based on 100 mass % of the protein fiber. Within this range, disperse uniformity will be high. The colorant of the present invention does not contain hematin, Sudan red, Nile red (all of them are pigments), or Green Fluorescent Protein (GFP) because these pigments have a problem in dispersibility with respect to a spinning solution, and GFP is expensive.

(1a) Acid dye: an acid dye is a dye for dyeing silk, wool, and nylon fibers. The acid dye includes a sodium salt of a color acid containing an acidic group such as a sulfonic acid group and a carboxyl group, and is expressed by general formulae: D-$SO_3$Na, D-COONa (where D is a dye base).

(1b) Basic dye: a basic dye is a dye for dyeing silk and wool. —$NH_2$, —NHR, —NR (R is an alkyl group with a carbon number of 1 to 3) substituted by an aromatic ring form an acid component and a salt such as a hydrochloric acid, and the general formula is expressed by D-$NH_3^+Cl^-$. A cationic dye that dyes an acrylic-based synthetic fiber well and that has high lightfastness also is a basic dye. When the basic dye is applied to the present invention, an increase in the viscosity of the spinning solution is observed.

(1c) Fluorescent dye: a fluorescent dye has a property of absorbing ultraviolet rays and emitting light of bluish purple having a wavelength longer than that of the ultraviolet rays. The fluorescent dye is used to remove yellowing of fibers to make the fibers look white. When the fluorescent dye is applied to the solution-dyed fiber of the polypeptide derived from spider silk proteins alone of the present invention, strong fluorescent colors are exhibited. Hence, it is suitably used for outerwear worn at night, a marker, an article tag, and the like.

(1d) Direct dye: a direct dye is a dye for dyeing silk and wool. The direct dye includes a sodium salt of a color acid containing a sulfonic acid group, and expressed by a general formula: D-$SO_3$Na.

(1e) Disperse dye: a disperse dye is a dye used in a state of being dispersed in water in a fine particulate state by a dispersant (surfactant). Most of the disperse dyes are anthraquinone-based dyes. The molecular weight is relatively small. When the disperse dye is applied to the present invention, the coagulation bath is contaminated.

(1f) Plant pigment: examples of the plant pigment include a safflower yellow pigment, a gardenia yellow pigment, a gardenia blue pigment, a paprika pigment, an annatto pigment, a β-carotene pigment, a cacao pigment, and anthocyanin-based pigments. The plant pigment is safe to a human body, and approved as a food natural pigment. When the plant pigment is applied to the solution-dyed fiber of the present invention, the obtained fiber can be used for sutures for surgery, and the like.

(1 g) Food natural pigment: examples of the food natural pigment include, in addition to the above plant pigments, a caramel pigment, a monascus pigment, a lac pigment, a cochineal pigment, a plant carbon pigment, and the like. Similarly to the plant pigment, the food natural pigment can be used for sutures for surgery, and the like.

(1h) Carbon black: carbon black is useful to color protein fibers black. A black solution-dyed protein fiber is suitable for artificial hair.

(2) Solution for Dissolving or Dispersing Colorant

Preferable examples of a solution for dissolving or dispersing a colorant include dimethyl sulfoxide (DMSO), N,N-dimethylformamide (DMF), hexafluoroisopropanol (HFIP), and hexafluoroacetone (HFA). Among these, in terms of cost and handleability, DMSO or DMF is preferred. DMSO has a melting point of 18.4° C. and a boiling point of 189° C. DMF has a melting point of −61° C. and a boiling point of 153° C. DMSO and DMF have much higher boiling points than hexafluoroisopropanol (HFIP) and hexafluroacetone (HFAc) having boiling points of 59° C. and −26.5° C., respectively, which have been used in conventional methods. Further, in view of the fact that DMSO and DMF have been used also in general industrial fields for acrylic fiber polymerization and acrylic fiber spinning solutions, etc., and as solvents for polyimide polymerization, they are low cost substances with proven safety. Addition of an inorganic salt to DMSO or DMF further increases the solubility of a solute. The inorganic salt is at least one selected from alkali metal halides (e.g., LiCl, LiBr, etc), alkaline-earth metal halides (e.g., $CaCl_2$), alkaline-earth metal nitrate (e.g., $Ca(NO_3)_2$, etc.), and sodium thiocyanate (e.g., NaSCN, etc.). When dissolution components are assumed to be 100 mass %, the percentage of the inorganic salt preferably ranges from 0.1 to 20 mass %. When an inorganic salt is added, it remains in a small amount in the finally-obtained solution-dyed protein fibers. A colorant is dissolved or dispersed in the solution in advance. Next, it is mixed with a spinning solution, or a solvent used for a spinning solution is added thereto, and thereafter protein powder having an ability to form fibers is added to the mixture, whereby a spinning solution is prepared.

(3) Silk Fibroin

Figure 4A:
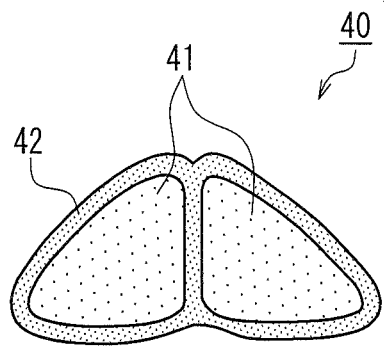
FIG. 4A is a schematic cross-sectional view of a cocoon filament of a domesticated silkworm.
Figure 4B:
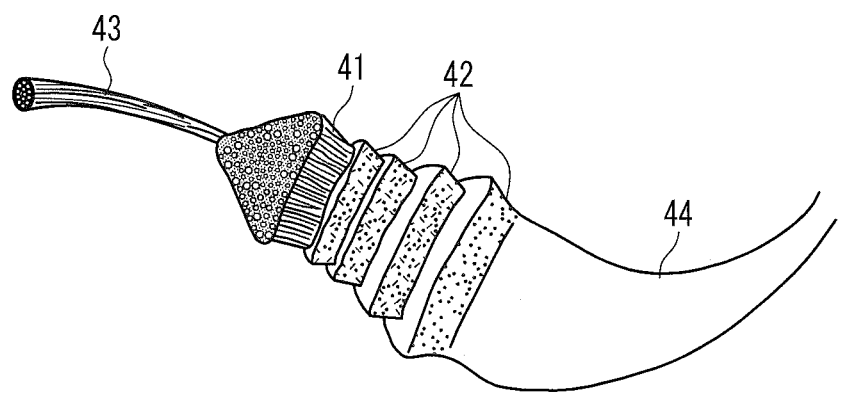
FIG. 4B is a schematic explanatory view showing a configuration of a cocoon filament of a domesticated silkworm.

Silk is a fiber obtained from a cocoon produced by a silkworm, which is a larva of *Bombyx mori*. As shown in the schematic cross-sectional view of a cocoon filament of a domesticated silkworm in FIG. 4A, two fibroins 41 are covered with an outer sticky substance (sericin) 42 to form one cocoon filament 40. Specifically, as the configuration of a cocoon filament of a domesticated silkworm shown in FIG. 4B, the fibroin 41 is composed of a plurality of fibrils 43, and the outer side of the fibroin 41 is covered with the sericin 42 having four layers, thereby configuring one cocoon filament 44. For practical use, the outer sericin 42 was dissolved and removed by scouring so that a cocoon filament is used as a silk filament for clothing use. The specific gravity of silk is 1.33. Further, generally, silk has an average fineness of 3.3 decitex and a fiber length of about 1300 to 1500 m. The reason for indicating the fineness as the "average fineness" is that the fineness of the cocoon filament is thick in the outer layer of the cocoon but it becomes thinner toward the inner side, which results in an uneven fineness of the filament as a whole. The silk fibroin used in the present invention is preferably obtained by: using a natural or domesticated cocoon, or a used or waste silk cloth as a raw material; removing sericin covering the silk fibroin and other substances such as fat therefrom; and purifying the silk fibroin to prepare silk fibroin freeze-dried powder.

(4) Polypeptide Derived from Spider Silk Proteins

The protein fiber of the present invention may be a polypeptide derived from spider silk proteins. The polypeptide derived from spider silk proteins is not limited particularly as long as it is derived from natural spider silk proteins or an analog of the natural spider silk proteins. In terms of excellent tenacity, the polypeptide is preferably derived from major dragline silk proteins produced in major ampullate glands of spiders. Examples of the major dragline silk proteins include major ampullate spidroin MaSp1 and MaSp2 derived from Nephila clavipes, and ADF3 and ADF4 derived from Araneus diadematus, etc.

The recombinant spider silk proteins may be derived from minor dragline silk produced in minor ampullate glands of spiders. Examples of the minor dragline silk proteins include minor ampullate spidroin MiSp1 and MiSp2 derived from Nephila clavipes.

Other than these, the recombinant spider silk proteins may be derived from flagelliform silk proteins produced in flagelliform glands of spiders. Examples of the flagelliform silk proteins include flagelliform silk proteins derived from Nephila clavipes, etc.

Examples of the polypeptide derived from major dragline silk proteins include a polypeptide containing two or more units of an amino acid sequence represented by the formula 1: REP1-REP2 (1), preferably a polypeptide containing four or more units thereof, and more preferably a polypeptide containing six or more units thereof. In the polypeptide derived from major dragline silk proteins, units of the amino acid sequence represented by the formula (1): REP1-REP2 (1) may be the same or may be different from each other. In the formula (1), the REP1 represents polyalanine.

In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 14 or less, and particularly preferably 12 or less. In the formula (1), the REP2 is an amino acid sequence composed of 10 to 200 amino acid residues. The total number of glycine, serine, glutamine, proline and alanine residues contained in the amino acid sequence is 40% or more, preferably 50% or more, and more preferably 60% or more with respect to the total number of amino acid residues contained therein.

In the major dragline silk, the REP1 corresponds to a crystal region in a fiber where a crystal β sheet is formed, and the REP2 corresponds to an amorphous region in a fiber where most of the parts lack regular configurations and that has more flexibility. Further, the [REP1-REP2] corresponds to a repetitious region (repetitive sequence) composed of the crystal region and the amorphous region, which is a characteristic sequence of dragline silk proteins.

An example of the polypeptide containing two or more units of the amino acid sequence represented by the formula 1: REP1-REP2 (1) is a recombinant spider silk protein derived from ADF3 having an amino acid sequence represented by any of SEQ ID NO: 1, SEQ ID NO: 2 and SEQ ID NO: 3. The amino acid sequence represented by SEQ ID NO: 1 is an amino acid sequence obtained by the following mutation: in an amino acid sequence of ADF3 to the N-terminal of which has been added an amino acid sequence (SEQ ID NO: 4) composed of a start codon, His 10 tags and an HRV3C Protease (Human rhinovirus 3C Protease) recognition site, $1^{st}$ to $13^{th}$ repetitive regions are about doubled and the translation ends at the $1154^{th}$ amino acid residue. The amino acid sequence represented by SEQ ID NO: 2 is an amino acid sequence obtained by adding the amino acid sequence (SEQ ID NO: 4) composed of a start codon, His 10 tags and an HRV3C Protease (Human rhinovirus 3C Protease) recognition site, to the N-terminal of a partial amino acid sequence of ADF3 (NCBI Genebank Accession No.: AAC47010, GI: 1263287) obtained from the NCBI database. The amino acid sequence represented by SEQ ID NO: 3 is an amino acid sequence obtained by the following mutation: in an amino acid sequence of ADF3 to the N-terminal of which has been added the amino acid sequence (SEQ ID NO: 4) composed of a start codon, His 10 tags and an HRV3C Protease (Human rhinovirus 3C Protease) recognition site, $1^{st}$ to $13^{th}$ repetitive regions are about doubled. Further, the polypeptide containing two or more units of the amino acid sequence represented by the formula 1: REP 1-REP2 (1) may be a polypeptide that is composed of an amino acid sequence represented by any of SEQ ID NO: 1, SEQ ID NO: 2 and SEQ ID NO: 3 in which one or a plurality of amino acids have been substituted, deleted, inserted and/or added and that has a repetitious region composed of a crystal region and an amorphous region.

In the present invention, "one or a plurality of" refers to 1 to 40, 1 to 35, 1 to 30, 1 to 25, 1 to 20, 1 to 15, 1 to 10, or 1 or a few, for example. Further, in the present invention, "one or a few" refers to 1 to 9, 1 to 8, 1 to 7, 1 to 6, 1 to 5, 1 to 4, 1 to 3, 1 to 2, or 1.

An example of the recombinant spider silk protein derived from minor dragline silk proteins is a polypeptide containing an amino acid sequence represented by the formula 2: REP3 (2). In the formula 2, the REP 3 indicates an amino acid sequence composed of (Gly-Gly-Z)m(Gly-Ala)l(A)r, where Z indicates any one of amino acids, particularly, it is preferably an amino acid selected from the group consisting of Ala, Tyr and Gln. Further, m is preferably 1 to 4, l is preferably 0 to 4, and r is preferably 1 to 6.

Among spider silks, the minor dragline silk is wound spirally from the center of a spider net, and used as a reinforcement of the net and as a yarn to wrap a captured prey. The minor dragline silk is inferior to the major dragline silk in tensile strength, but is known to have high stretchability. The reason for this is considered to be that since in the minor dragline silk, many crystal regions are formed from a region in which glycine and alanine are arranged alternately in succession, hydrogen bonds of the crystal regions weaken easily as compared with the major dragline silk whose crystal regions are formed only of alanine.

Examples of the recombinant spider silk protein derived from flagelliform silk proteins include a polypeptide containing an amino acid sequence represented by the formula 3: REP4 (3). In the formula 3, the REP 4 Indicates an amino acid sequence composed of (Gly-Pro-Gly-Gly-X)n, where X indicates any one of amino acids, particularly, it is preferably an amino acid selected from the group consisting of Ala, Ser, Tyr and Val. Further, n indicates a number at least equal to or larger than 4, preferably 10 or larger, and more preferably 20 or larger.

Among spider silks, the flagelliform silk does not have a crystal region, but has a repetitious region composed of an amorphous region, which is a major characteristic of the flagelliform silk. Since the major dragline silk and the like have a repetitious region composed of a crystal region and an amorphous region, they are expected to have both high stress and stretchability. Meanwhile, as to the flagelliform silk, although the stress is inferior to that of the major dragline silk, the stretchability is high. The reason for this is considered to be that most of the flagelliform silk is composed of amorphous regions.

(5) Mixing Ratio of Silk Fibroin and Polypeptide Derived from Spider Silk Proteins The protein fiber of the present invention may be composed of either silk fibroin alone, a polypeptide derived from spider silk proteins alone, or a mixed composition of the silk fibroin and the polypeptide derived from spider silk proteins. In the case of the mixed composition, the silk fibroin can be mixed in a range of 0 to 100 mass %, and the polypeptide derived from spider silk proteins can be mixed in a range of 0 to 100 mass %. Within this ratio, the protein fiber will have favorable spinnability, have good affinity between these components without separation, and be a hybrid protein fiber, and have high stress and appropriate rupture elongation.

(6) Spinning Solution (Dope Solution)

As a solvent for the silk fibroin freeze-dried powder and polypeptide freeze-dried powder derived from spider silk proteins, any solvent can be used as long as it can dissolve polypeptides. Examples of the solvent include an aqueous solution containing hexafluoroisopropanol (HFIP), hexafluoroacetone (HFA), urea, guanidine, sodium lauryl sulfate (SDS), lithium bromide, calcium chloride, lithium thiocyanate or the like, dimethyl sulfoxide (DMSO), DMSO to which an inorganic salt is added, N,N-dimethylformamide (DMF), DMF to which an inorganic salt is added. Among these, in terms of cost and handleability, dimethyl sulfoxide (DMSO), DMSO to which an inorganic salt is added, N,N-dimethylformamide (DMF), DMF to which an inorganic salt is added are preferred. The concentration of the protein is preferably 4.2 to 15.8 mass %. The inorganic salt is at least one selected from alkali metal halides (e.g., LiCl, LiBr, etc), alkaline-earth metal halides (e.g., $CaCl_2$), alkaline-earth metal nitrate (e.g., $Ca(NO_3)_2$, etc.), and sodium thiocyanate (e.g., NaSCN, etc.). When dissolution components are assumed to be 100 mass %, the percentage of the inorganic salt preferably ranges from 0.1 to 20 mass %. Dusts and bubbles are removed so as to prepare a spinning solution (dope solution) having a viscosity of 2,500 to 15,000 cP (centipoises).

(7) Spinning Process

Wet spinning is adopted for spinning. By this method, the solvent dissolving a polymer is removed (also called as desolvation), and an undrawn yarn is obtained. A coagulation liquid used for wet spinning is not limited particularly as long as it is a solution allowing desolvation. When the solvent is HFIP, the coagulation liquid is preferably a lower alcohol with a carbon number of 1 to 5, such as methanol, ethanol and 2-propanol. The temperature of the coagulation liquid is preferably 0° C.-30° C. This range stabilizes spinning. By extruding the above spinning solution into the coagulation liquid, an undrawn yarn is obtained. In the case of a syringe pump with a nozzle 0.57 mm in diameter, the extrusion speed is preferably 0.2-5.0 ml/h per one hole. This range stabilizes spinning. A more preferable extrusion speed is 0.25-3 ml/h per one hole. It is preferable that the length of the coagulation liquid tank is 200-500 mm, the take-up speed of the undrawn yarn is 1-20 m/min, and the residence time is 0.05-3 minutes. These ranges allow efficient desolvation. Drawing (pre-drawing) may be performed in the coagulation liquid. However, taking into consideration the evaporation of a lower alcohol, it is preferable to maintain the coagulation liquid at low temperature and take up yarns in an undrawn state. The coagulation liquid tank may be provided in plural stages, and drawing may be performed therein.

(8) Drawing Process

In a drawing process, an undrawn yarn is preferably drawn to 1.05 to 4 times under dry heat at a draw temperature of 160° C. to 230° C. In the present invention, by performing high-temperature dry heating as described above, molecules are oriented highly and a drawn yarn with high strength can be obtained. A preferable draw temperature is 160° C. to 180° C. A preferable draw ratio is 1.05 to 1.5 times. As one example, an electric tubular furnace or a dry-heat plate is used for dry heating.

(8a) Continuous Drawing Process

The process from spinning to drawing may be performed continuously, or may be divided into any processes. FIG. 1 is an explanatory view showing a production process in one example of the present invention. FIG. 1 shows a continuous process. A spinning-drawing device 10 includes an extrusion process 1, an undrawn-yarn production process 2, and a dry-heat drawing process 3. A spinning solution 6 is stored in a storage tank 7 and extruded from a gear pump 8 to a spinneret 9. In a laboratory scale, a spinning solution may be filled in a cylinder and extruded from a nozzle using a syringe pump. The extruded spinning solution is supplied directly or via an air gap 13 into a coagulation liquid 11 in a coagulation liquid tank 12, so as to remove a solvent. Thereafter, an obtained undrawn yarn is supplied to a dry-heat drawing device 17 and drawn inside a guide 18, whereby a yarn roll 4 is obtained. The drawing depends on the speed ratio between a supply nip roller 15 and a take-up nip roller 16. The reference numerals 14a to 14f indicate yarn guides.

(8b) Separate Drawing Process

Figure 2A:
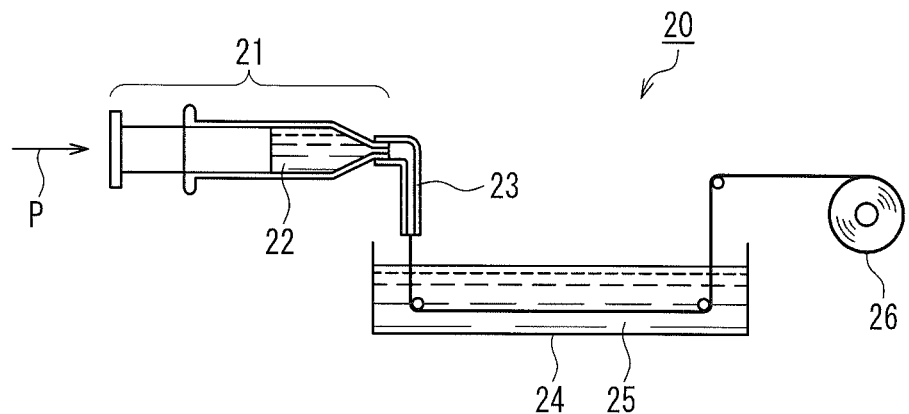
FIGS. 2A and 2B are explanatory views showing a production process in another example of the present invention.
Figure 2B:
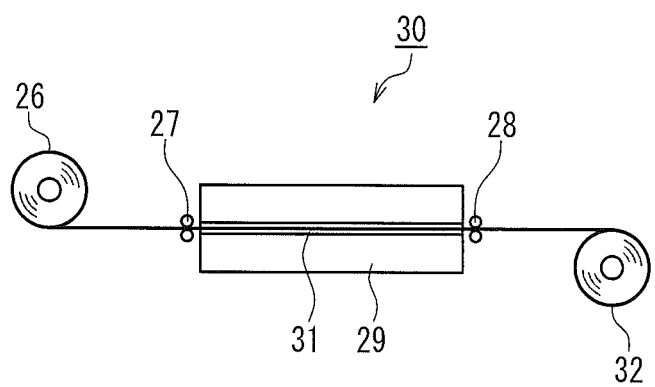

FIGS. 2A and 2B are explanatory views in another example of the present invention in which the production process is separated. FIG. 2A shows a spinning process 20, and FIG. 2B shows a dry-heat drawing process 30. In each process, a yarn may be wound, or may be stored in a container without being wound. In the spinning process 20, a spinning solution 22 is contained in a microsyringe 21 and moved in a direction indicated by an arrow P using a syringe pump, thereby being extruded from a nozzle 23 and supplied into a coagulation liquid 25 in a coagulation liquid tank 24. Thus, a yarn roll 26 of an undrawn yarn is obtained. Next, in the dry-heat drawing process 30, the undrawn yarn is unwound from the yarn roll 26, supplied to a dry-heat drawing device 29, and drawn inside a guide 31. The drawing depends on the speed ratio between a supply nip roller 27 and a take-up nip roller 28. Then, the drawn yarn is wound as a yarn roll 32. Thus, a drawn yarn of a fibroin fiber of the present invention is obtained.

(8c) Water-Bath Drawing Process

Figure 3:
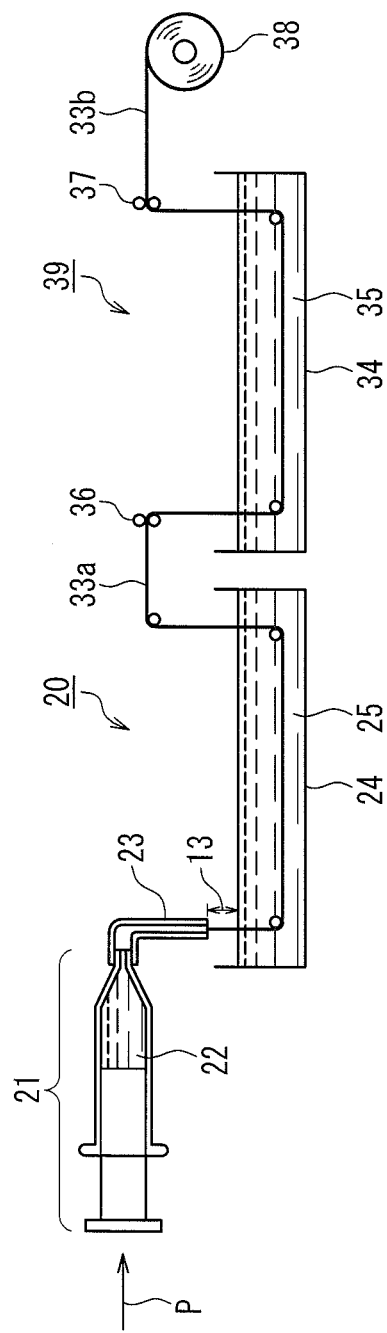
FIG. 3 is an explanatory view showing a production process in still another example of the present invention.

In the method of the present invention, before the dry-heating drawing, an undrawn yarn can be drawn in a water bath in advance. The water-bath drawing allows the orientation of molecules to be enhanced further. The water-bath drawing is useful also for a mixture (hybrid) of the silk fibroin and the spider silk protein. The conditions for the water-bath drawing are preferably at a temperate of 30° C. to 90° C. and a draw ratio of 1.05 to 6 times. FIG. 3 shows a water-bath drawing process. The process is the same as that in FIG. 2A until the coagulation process. An undrawn yarn 33a having passed through the coagulation process passes a nip roller 36, enter a water bath 35 in a water-bath tank 34, and is drawn by a nip roller 37. Thus, a drawn yarn 33b is obtained and wound as a yarn roll 38. The reference numeral 39 indicates a water-bath drawing process. A drawn yarn having passed through the water-bath drawing process 39 is drawn in the dry-heat drawing process 30 shown in FIG. 2B.

The single fiber diameter of the solution-dyed fiber of the present invention preferably ranges from 5 to 200 μm. Within this range, drawn fibers can be obtained stably. Yarns having a high fineness are suitable for artificial hair. The fiber diameter more preferably ranges from 7 to 100 μm, and further preferably ranges from 10 to 80 μm. In the case of calculating the fineness (unit: tex or decitex), when the fiber is round in cross section, the fineness is calculated from a cross-sectional area obtained from the fiber diameter, a specific gravity, and a length. Incidentally, since the fiber of the present invention is obtained by wet spinning, the cross section is not limited to the round shape, and may be in various shapes. Therefore, the fiber diameter (average diameter) as used herein refers to an average diameter based on the assumption that the cross section is round.

EXAMPLES

Hereinafter, the present invention will be described in further detail by way of examples. Note that the present invention is not limited to the following examples.

Examples 1-5, Comparative Examples 1-2

1. Preparation of Silk Fibroin Raw Material (1) A silk cloth was cut into pieces of about 2 mm×10 mm, and heated for about 30 minutes in 0.5 mass % of boiling Marseilles soap water (Marseilles soap was grated by a grater for use).

(2) Thereafter, the pieces were heated for 30 minutes in boiling water.

(3) The steps 1 and 2 were repeated two more times (three times in total).

(4) Finally, the resultant was heated for 30 minutes in boiling water. By this procedure, sericin covering silk fibroin and other additives were removed completely.

(5) The wet silk fibroin was dried overnight under an atmosphere of 37° C.

(6) The silk fibroin after drying was weighed, and an LiBr aqueous solution (9 mol/L) was added thereto so that the content of the silk fibroin would be 10 w/v %. The silk fibroin was dissolved for 2 hours under an atmosphere of 40° C.

(7) The aqueous solution was placed in a cellulose dialysis membrane (manufactured by VISKASE SALES CORPORATION, Seamless Cellulose Tubing, 36/32), and dialyzed with distilled water for 3 to 4 days.

(8) The collected solution after dialysis was centrifuged for 1 hour at 15,000 rpm at 20° C., so as to remove undissolved residue, dusts, and the like.

(9) Further, the solution was diluted with MilliQ so that the concentration would be 2 mass % or lower.

(10) After dilution, the solution was filtered using a 150 μm filter manufactured by ADVANTEC Co. Ltd., so as to remove fine dusts completely.

(11) The obtained silk fibroin aqueous solution was frozen under an atmosphere of −80° C., and freeze-dried overnight. After checking that water was removed completely, it was stored as silk fibroin powder. Thus, silk fibroin freeze-dried powder was obtained.

2. Preparation of Polypeptide Derived from Spider Silk Proteins

<Gene Synthesis>
(1) Gene Synthesis of ADF3Kai

A partial amino acid sequence of ADF3 (GI: 1263287), which is one of two principal dragline silk proteins of Araneus diadematus, was obtained from the NCBI web database, and synthesis of a gene encoding an amino acid sequence (SEQ ID NO: 2) was outsourced to GenScript, Inc. The amino acid sequence (SEQ ID NO: 2) is an amino acid sequence obtained by adding an amino acid sequence (SEQ ID NO: 4) composed of a start codon, His 10 tags and an HRV3C Protease (Human rhinovirus 3C Protease) recognition site, to the N-terminal of said partial amino acid sequence of ADF3. Consequently, a pUC57 vector to which a gene of ADF3Kai having a base sequence represented by SEQ ID NO: 5 had been introduced was obtained (having an Nde I site immediately upstream of 5' terminal of the gene and an Xba I site immediately downstream of 5' terminal thereof). Thereafter, the gene was subjected to a restriction enzyme treatment with Nde I and EcoR I, and recombined into a pET22b(+) expression vector.

(2) Gene Synthesis of ADF3Kai-Large

The half of the gene sequence of ADF3Kai on the 5' side (hereinafter, referred to as a sequence A) was amplified by the PCR reaction using ADF3Kai as a template, and a T7 promoter primer (SEQ ID NO: 8) and a Rep Xba I primer (SEQ ID NO: 9). The obtained DNA fragment of the sequence A was recombined into a pUC118 vector that in advance had been subjected to the restriction enzyme treatment with Nde I and Xba I using a Mighty Cloning Kit (manufactured by TAKARA BIO INC.). Similarly, the half of the gene sequence of ADF3Kai on the 3' side (hereinafter, referred to as a sequence B) was amplified by the PCR reaction using ADF3Kai as a template, and an Xba I Rep primer (SEQ ID NO: 10) and a T7 terminator primer (SEQ ID NO: 11). The obtained DNA fragment of the sequence B was recombined into a pUC118 vector that in advance had been subjected to the restriction enzyme treatment with Xba I and EcoR I using the Mighty Cloning Kit (manufactured by TAKARA BIO INC.). The pUC118 vector to which the sequence A had been introduced and the pUC118 vector to which the sequence B had been introduced were subjected to the restriction enzyme treatment with Nde I, Xba I and Xba I, EcoR I, respectively, and target DNA fragments of the sequences A and B were purified by gel cut. The DNA fragments A, B and the pET22b(+) that in advance had been subjected to the restriction enzyme treatment with Nde I and EcoR I were subjected to a ligation reaction and transformed into Escherichia coli DH5a. After confirming the insertion of the target DNA fragments by a colony PCR using a T7 promoter primer and a T7 terminator primer, plasmid was extracted from a colony where a target band size (3.6 kbp) was obtained, and the entire base sequence was checked by a sequence reaction using a 3130×1 Genetic Analyzer (Applied Biosystems). Consequently, the construction of a gene of ADF3Kai-Large represented by SEQ ID NO: 6 was confirmed. The amino acid sequence of ADF3Kai-Large is as represented by SEQ ID NO: 3.

(3) Gene Synthesis of ADF3Kai-Large-NRSH1

With a pET22b(+) vector to which the gene of ADF3Kai-Large obtained above had been introduced used as a template, through Site-Directed Mutagenesis using a PrimeSTAR Mutagenesis Basal Kit (manufactured by TAKARA BIO INC.), a codon GGC corresponding to the 1155$^{th}$ amino acid residue, i.e., glycine (Gly), in the amino acid sequence of ADF3Kai-Large (SEQ ID NO: 3) was mutated into a stop codon TAA, and a gene of ADF3Kai-Large-NRSH1 represented by SEQ ID NO: 7 was constructed on the pET22b(+). The accuracy of the introduction of the mutation was checked by the sequence reaction using the 3130×1 Genetic Analyzer (Applied Biosystems). The amino acid sequence of ADF3Kai-Large-NRSH1 is as represented by SEQ ID NO: 1.

<Expression of Protein>

The pET22b(+) expression vector containing the gene sequence of ADF3Kai-Large-NRSH1 was transformed into Escherichia coli Rosetta (DE3). The obtained single colony was incubated for 15 hours in 2 mL of an LB culture medium containing ampicillin. Thereafter, 1.4 ml of said culture solution was added to 140 mL of an LB culture medium containing ampicillin, and incubated to an OD$_{600}$ of 3.5 under the conditions of 37° C. and 200 rpm. Next, the culture solution with the OD$_{600}$ of 3.5 was added to 7 L of a 2xYT culture medium containing ampicillin together with 140 mL of 50% glucose, and incubated further to the OD$_{600}$ of 4.0. Thereafter, isopropyl-β-thiogalactopyranoside (IPTG) was added to the obtained culture solution with the $OD_{600}$ of 4.0 so that the final concentration became 0.5 mM, thereby inducing the expression of protein. After a lapse of two hours from the addition of IPTG, the culture solution was centrifuged and bacterial cells were collected. Protein solutions prepared from the culture solutions before the addition of IPTG and after the addition of IPTG were each electrophoresed in a polyacrylamide gel. Consequently, a target band size (about 101.1 kDa) was observed with the addition of IPTG, and the expression of the target protein was confirmed.

Purification (1) About 50 g of bacteria cells of the *Escherichia coli* expressing the ADF3Kai-Large-NRSH1 protein and 300 ml of a buffer solution M (20 mM Tris-HCl, pH 7.4) were placed in a centrifuge tube (1000 ml). After dispersing the bacteria cells with a mixer ("T18 basic ULTRA TURRAX" manufactured by IKA, level 2), the dispersion was centrifuged (11,000 g, 10 minutes, room temperature) with a centrifuge ("Model 7000" manufactured by Kubota Corporation), and a supernatant was discarded.

(2) To a precipitate (bacteria cells) obtained by the centrifugation, 300 ml of the buffer solution M and 3 ml of 0.1 M PMSF (dissolved by isopropanol) were added. After dispersing the precipitate for 3 minutes with the above mixer (level 2) manufactured by IKA, the bacteria cells were disrupted repeatedly for three times using a high-pressure homogenizer ("Panda Plus 2000" manufactured by GEA Niro Soavi).

(3) To the disrupted bacterial cells, 300 mL of a buffer solution B (50 mM Tris-HCL, 100 mM NaCl, pH 7.0) containing 3 w/v % of SDS was added. After dispersing well the bacterial cells with the above mixer (level 2) manufactured by IKA, the dispersion was stirred for 60 minutes with a shaker (manufactured by TAITEC CORPORATION, 200 rpm, 37° C.). Thereafter, the stirred dispersion was centrifuged (11,000 g, 30 minutes, room temperature) with the above centrifuge manufactured by Kubota Corporation, and a supernatant was discarded, whereby SDS washing granules (precipitate) were obtained.

(4) The SDS washing granules were suspended in a DMSO solution containing 1M lithium chloride so that the concentration would be 100 mg/mL, and heat-treated for 1 hour at 80° C. Thereafter, the heated suspension was centrifuged (11,000 g, 30 minutes, room temperature) with the above centrifuge manufactured by Kubota Corporation, and a supernatant was collected.

(5) Ethanol in an amount three times as much as the collected supernatant was prepared. The collected supernatant was added to the ethanol, and left to stand for 1 hour at room temperature. Thereafter, the resultant was centrifuged (11,000 g, 30 minutes, room temperature) with the above centrifuge manufactured by Kubota Corporation to collect aggregated protein. Next, a process of washing aggregated protein using pure water and a process of collecting aggregated protein by centrifugation were repeated three times, and thereafter water was removed by a freeze dryer to collect freeze-dried powder. The purification degree of the target protein ADF3Kai-Large-NRSH1 (about 56.1 kDa) in the obtained freeze-dried powder was checked by analyzing images of the results of polyacrylamide gel electrophoresis (CBB staining) of said protein powder using Totallab (non-linear dynamics Ltd.). As a result, the purification degree of ADF3Kai-Large-NRSH1 was about 85%.

3. Adjustment of Colorant

As a colorant, Acid Milling Sky Blue FSE (manufactured by Nippon Kayaku Co., Ltd.), which is a fiber acid dye, was weighed so that the dye concentration per fiber's dry mass (product mass) would be 1 mass %. First, 20 mass % of the acid dye was dissolved or dispersed in dimethyl sulfoxide (DMSO). The acid dye was easily dissolved or dispersed in DMSO, but was not dissolved or dispersed in hexafluoroisopropanol (HFIP) at all. To 5 mass % of the DMSO solution in which the acid dye was dissolved, 95 mass % of hexafluoroisopropanol (HFIP) was added and mixed. DMSO and HFIP are dope solvents for dissolving the silk fibroin powder and the polypeptide powder derived from spider silk proteins.

4. Preparation of Spinning Solution (Dope Solution)

(1) Examples 1-5

In Examples 1-5, the silk fibroin powder after freeze-drying and the polypeptide powder derived from spider silk proteins after freeze-drying were weighed, and dissolved so that the total powder concentration would be in the following percentages to prepare respective dope solutions. DMSO was used as a solvent for preparing the dope solutions.
(a) silk 100% and silk:spider=75:25, 6.3 (w/w) %
(b) silk:spider=50:50, 7.5 (w/w) %
(c) silk:spider=25:75, 8.6 (w/w) %
(d) spider 100%, 12.9 (w/w) %

After 16 hours of dissolution using a shaker, dusts and bubbles were removed to produce spinning solutions (dope solutions). The viscosity of the dope solutions was 4,500 cP (centipoises).

(2) Comparative Examples 1-2

In Comparative Examples 1-2, spinning solutions (dope solutions) were produced in the same manner as in Examples 1-5 except that dyes were not added therein. The viscosity of the dope solutions was 4,500 cP (centipoises).

5. Spinning Process

The method shown in FIG. 3 was adopted as the spinning process. First, the spinning solution (dope solution) was filled in a cylinder and extruded from a nozzle 0.2 mm in diameter using a syringe pump, whereby an undrawn yarn was produced in a 100 mass % methanol coagulation liquid. The extrusion speed was 2.0 to 2.5 ml/h. The length of the coagulation liquid tank was 400 mm, and the length of the water-bath drawing tank also was 400 mm. The draw ratio in the coagulation liquid tank was 1.5 times, and the draw ratio in the water-bath drawing tank was 2 times.

6. Drawing Process

The method shown in FIG. 2B was adopted as the drawing process. The drawn yarn obtained above was further drawn with dry heat using a dry-heat plate. The length of the dry-heat plate was 500 mm, and the draw ratio was 1.05 to 1.5 times. The draw temperature was as follows.
(a) silk 100% and silk:spider=75:25, 160° C.
(b) silk:spider=50:50, 170° C.
(c) silk:spider=25:75, 180° C.
(d) spider 100%, 180° C.

7. Physical Property Measurement (1) The fiber diameter was measured using an optical microscope.
(2) The strength, the initial elastic modulus (obtained based on the measurement of inclinations of 20 points:

inclinations were measured at 20 points with an interval of 50 msec and the maximum inclination was defined as the initial elastic modules), and the elongation of the fiber were measured using a tensile tester (small table-top tester EZ-S manufactured by Shimadzu Corporation) under an ambient temperature of 25° C. and a relative humidity of 60%, and the toughness was calculated. The sample was attached to a cardboard form, the distance between grippers was 20 mm, and the tensile speed was 10 mm/min. The load cell capacity was 1 N, and the gripper was a clip type. The measured value was an average of five samples (n=5). The formula for calculating toughness was as follows:

$$\text{Toughness} = [E/(r^2 \times \pi \times L) \times 1000] \text{(unit: MJ/m}^3\text{)},$$

where
E Fracture energy (unit: J)
r Fiber radius (unit: mm)
π Pi
L Distance between grippers in tensile test measurement: 20 mm (3) The measurement of the specific gravity of fibers was outsourced to KAKEN TEST CENTER, and performed in accordance with JIS L 1015, a float-and-sink method. Each of the products of Examples 1-5 had a specific gravity of 1.36.

8. Measurement of Remaining Amount of Solvent

In Example 33, the remaining amount of the solvent was measured. As an internal standard, 1,2-dichloroethane-formic acid solution at a concentration of 3,100 ppm (0.00310 mg/mi.) was prepared. 500 µl of a protein solution (0.1 g of the solution-dyed fiber was dissolved in 10 ml of formic acid) and 500 µl of an internal standard solution were mixed. Further, an acetonitrile deuterated solvent for H-NMR measurement in an amount approximately equivalent to the mixture solution was added to the mixed solution so as to dilute the solution to about two times, and H-NMR measurement was performed (the model of NMR: JNM-ECX 100 manufactured by JOEL Ltd.). The H-NMR integrated intensity of 1,2-dichloroethane (internal standard sample) was compared with the H-NMR integrated intensity of DMSO. A calibration curve was formed by preparing a DMSO-formic acid solution at 3 ppm to 3000 ppm and following the above protocol. By comparison with the calibration curve, the concentration of DMSO in the protein solution was calculated. For the measurement of the concentration of DMSO, a nuclear magnetic resonator (NMR) manufactured by JOEL Ltd. was used.

Table 1 summarizes the conditions and results of Examples 1-5 and Comparative Examples 1-2.

TABLE 1

| Experiment No. | Ratio of silk:spider (mass %) | Addition amount of acid dye (mass %) | Single fiber diameter (µm) | Max. stress (MPa) | Average stress (MPa) | Elastic modulus (GPa) | Strain (%) | Toughness (MJ/m³) | Color tone (naked-eye observation) |
|---|---|---|---|---|---|---|---|---|---|
| Comparative Example 1 | Silk 100 | 0 | 33.8 | 410.3 | 386.6 | 8.4 | 8.8 | 22.9 | Transparent white with luster |
| Example 1 | Silk 100 | 1 | 33.8 | 421.3 | 406.8 | 8.4 | 9.3 | 25.0 | Bright blue with luster |
| Example 2 | Silk 75 Spider 25 | 1 | 35.5 | 399.4 | 384.4 | 8.5 | 9.0 | 23.9 | Bright blue with metallic luster |
| Example 3 | Silk 50 Spider 50 | 1 | 37.5 | 325.9 | 314.2 | 7.1 | 8.2 | 17.7 | Bright blue with metallic luster |
| Example 4 | Silk 25 Spider 75 | 1 | 35.5 | 326.7 | 310.4 | 6.9 | 10.0 | 22.6 | Bright blue with metallic luster |
| Example 5 | Spider 100 | 1 | 45.5 | 233.7 | 225.6 | 5.5 | 15.1 | 27.0 | Bright blue without metallic luster |
| Comparative Example 2 | Spider 100 | 0 | 45.5 | 234.0 | 211.6 | 5.9 | 9.6 | 14.3 | White without luster |

(Note)
"Silk" is an abbreviation for silk fibroin, and "Spider" is an abbreviation for polypeptide derived from spider silk proteins. The same applied to the following.

As shown in Table 1, solution-dyed fibers with bright blue color were obtained in Examples 1-5. Especially in Examples 1-4, metallic luster was observed, and beautifully colored solution-dyed fibers were obtained.

Examples 6-8

In Examples 6-8, the addition amount of the acid dye was changed in the experiment. The experiment was performed in the same manner as in Examples 1-5 except that the ratio of the silk fibroin was 100 mass %, and the addition amount of the acid dye was changed. Table 2 summarizes the conditions and results.

TABLE 2

| Experiment No. | Ratio of silk:spider (mass %) | Addition amount of acid dye (mass %) | Single fiber diameter (µm) | Max. stress (MPa) | Average stress (MPa) | Elastic modulus (GPa) | Strain (%) | Toughness (MJ/m³) | Color tone (naked-eye observation) |
|---|---|---|---|---|---|---|---|---|---|
| Example 6 | Silk 100 | 0.1 | 34.4 | 402.4 | 385.5 | 10.7 | 13.9 | 42.0 | Bright blue with luster |
| Example 7 | Silk 100 | 0.5 | 34.6 | 413.8 | 388.9 | 10.9 | 7.4 | 19.4 | Bright blue with metallic luster |

TABLE 2-continued

| Experiment No. | Ratio of silk:spider (mass %) | Addition amount of acid dye (mass %) | Single fiber diameter (μm) | Max. stress (MPa) | Average stress (MPa) | Elastic modulus (GPa) | Strain (%) | Toughness (MJ/m³) | Color tone (naked-eye observation) |
|---|---|---|---|---|---|---|---|---|---|
| Example 8 | Silk 100 | 1 | 90.0 | 371.0 | 365.8 | 12.4 | 31.8 | 105.8 | Bright blue with metallic luster |

As shown in Table 2, solution-dyed fibers with bright blue color were obtained in Examples 6-8. The fineness of the fiber of Example 8 was thick enough to be applied as artificial hair. Solution-dyed fibers having such a thick fineness also can be produced.

Examples 9-12, Comparative Example 3

In Examples 9-12 and Comparative Example 3, the type of the fiber acid dye was changed in the experiment. The experiment was performed in the same manner as in Examples 1-5 except that the ratio of the silk fibroin was 80 mass %, the ratio of the spider silk protein was 20 mass %, and the following fiber acid dyes were used. Table 3 summarizes the conditions and results.

Blue acid dye for fiber: the same dye as that used in Examples 1-5
Purple acid dye for fiber: Kayanol milling Violet FBW (manufactured by Nippon Kayaku Co., Ltd.)
Red acid dye for fiber: Polar Red B 125% (manufactured by Huntsman International LLC.)
Black acid dye for fiber: Irgalan Black BGL 200% (manufactured by Huntsman International LLC.)

TABLE 3

| Experiment No. | Ratio of silk:spider (mass %) | Addition amount of acid dye (mass %) | Single fiber diameter (μm) | Max. stress (MPa) | Average stress (MPa) | Elastic modulus (GPa) | Strain (%) | Toughness (MJ/m³) | Color tone (naked-eye observation) |
|---|---|---|---|---|---|---|---|---|---|
| Comparative Example 3 | Silk 80 Spider 20 | 0 | 27.7 | 323.2 | 309.8 | 7.8 | 35.4 | 93.9 | Transparent white with luster |
| Example 9 | Silk 80 Spider 20 | Blue 1 | 35.0 | 339.9 | 334.5 | 8.4 | 41.6 | 118.5 | Bright blue with luster |
| Example 10 | Silk 80 Spider 20 | Purple 1 | 36.0 | 347.5 | 336.1 | 7.9 | 42.5 | 121.4 | Bright purple with metallic luster |
| Example 11 | Silk 80 Spider 20 | Red 2 | 32.0 | 392.1 | 376.0 | 9.5 | 16.2 | 50.8 | Bright red with metallic luster |
| Example 12 | Silk 80 Spider 20 | Black 2 | 29.4 | 356.1 | 320.1 | 7.6 | 30.1 | 81.2 | Dark black with metallic luster |

As shown in Table 3, solution-dyed fibers with bright color were obtained in Examples 9-11. Also, metallic luster was observed, and beautifully colored solution-dyed fibers were obtained.

Examples 13-19

In Examples 13-19, the type of the fiber acid dye was changed in the Lab colorimetric experiment. The experiment was performed in the same manner as in Examples 1-5 except that the ratio of the silk fibroin was 80 mass %, the ratio of the spider silk protein was 20 mass %, and the following acid dyes were used. Table 4 summarizes the conditions and results.

Blue acid dye for fiber: the same dye as that used in Examples 1-5
Purple acid dye for fiber: Kayanol milling Violet FBW (manufactured by Nippon Kayaku Co., Ltd.)
Red acid dye for fiber: Polar Red B 125% (manufactured by Huntsman International LLC.)
Black acid dye for fiber: Irgalan Black BGL 200% (manufactured by Huntsman International LLC.)
Yellow acid dye for fiber: Acid Yellow RW New (manufactured by Nippon Kayaku Co., Ltd.)

TABLE 4

| Experiment No. | Ratio of silk:spider (mass %) | Addition amount of acid dye (mass %) | L* | a* | b* | ΔE*ab |
|---|---|---|---|---|---|---|
| Example 13 | Silk 80 Spider 20 | Red 2 | 27.42 | 45.47 | 21.18 | 57.17 |
| Example 14 | Silk 80 Spider 20 | Yellow 0.5 | 60.36 | 27.64 | 75.87 | 100.81 |
| Example 15 | Silk 80 Spider 20 | Yellow 1 | 55.87 | 39.77 | 70.48 | 98.34 |
| Example 16 | Silk 80 Spider 20 | Blue 1 | 24.75 | 14.09 | −47.33 | 55.24 |
| Example 17 | Silk 80 Spider 20 | Purple 1 | 23.24 | 31.81 | −39.13 | 55.53 |
| Example 18 | Silk 80 Spider 20 | Black 1 | 21.38 | 0.18 | −0.27 | 21.38 |
| Example 19 | Silk 80 Spider 20 | Black 2 | 13.81 | 0.11 | −0.43 | 13.82 |

The solution-dyed fibers of respective colors shown in Table 4 had high brightness and exhibited metallic luster.

Example 20

In Example 20, a fiber fluorescent dye was used to prepare a solution-dyed fiber. The experiment was performed in the same manner as in Examples 1-5 except that the spider silk protein used in Examples 1-5 was adopted, and NKP-8315 Yellow (distributed by SEIKO TORYO CO., LTD.), which is a fiber fluorescent dye, was added as a colorant so that the product concentration would be 1 mass %. The obtained solution-dyed fiber (drawn yarn) had the following physical properties.

Diameter of single fiber: 42.7 μm
Maximum stress: 330.0 MPa
Average stress: 322.5 MPa
Elastic modulus: 5.8 GPa
Strain: 11.6%
Toughness: 26.4 MJ/m$^3$ The obtained solution-dyed fiber exhibited bright fluorescent color when irradiated with black light. The fluorescence was vivid just like light emitted by a fluorescent lamp.

Examples 21-23

In Examples 21-23, a natural plant pigment was used to prepare solution-dyed fibers. The experiment was performed in the same manner as in Examples 1-5 except that, as a colorant, safflower Y1500 (Daiwa Kasei Co., Ltd., water-soluble safflower yellow pigment), which is a natural plant pigment, was added and dissolved in hexafluoroisopropanol (HFIP) so that the product concentration would be 1 mass %. The obtained solution-dyed fibers (drawn yarns) had the following physical properties.

TABLE 5

| Experiment No. | Ratio of silk:spider (mass %) | Addition amount of dye (mass %) | Single fiber diameter (μm) | Max. stress (MPa) | Average stress (MPa) | Elastic modulus (GPa) | Strain (%) | Toughness (MJ/m$^3$) | Color tone (naked-eye observation) |
|---|---|---|---|---|---|---|---|---|---|
| Example 21 | Silk 100 | Natural pigment 1 | 34.3 | 399.7 | 382.2 | 9.7 | 8.7 | 22.9 | Transparent yellow with luster |
| Example 22 | Silk 50 Spider 50 | Natural pigment 1 | 33.6 | 368.0 | 341.2 | 8.6 | 10.9 | 28.2 | Bright yellow with metallic luster |
| Example 23 | Spider 100 | Natural pigment 1 | 40.9 | 235.7 | 221.1 | 5.9 | 9.5 | 15.1 | Yellow |

As shown in Table 5, the solution-dyed fibers of Examples 21-23 had color tone almost the same as that of the solution-dyed fibers to which the acid dye was added. However, the solution-dyed fiber of spider silk 100 mass % slightly lacked luster, had color muddiness, and whitening was observed.

Examples 24-26

In Examples 24-26, a fiber cationic dye was used to prepare solution-dyed fibers. The experiment was performed in the same manner as in Examples 1-5 except that Kayacryl Blue GSL-ED (manufactured by Nippon Kayaku Co., Ltd.), which is a cationic dye, was added as a colorant so that the product concentration would be 1 mass %. The obtained solution-dyed fibers (drawn yarns) had the following physical properties.

TABLE 6

| Experiment No. | Ratio of silk:spider (mass %) | Addition amount of dye (mass %) | Single fiber diameter (μm) | Max. stress (MPa) | Average stress (MPa) | Elastic modulus (GPa) | Strain (%) | Toughness (MJ/m$^3$) | Color tone (naked-eye observation) |
|---|---|---|---|---|---|---|---|---|---|
| Example 24 | Silk 100 | Cationic dye 1 | 40.8 | 402.0 | 382.1 | 9.7 | 8.6 | 22.9 | Dark blue with luster |
| Example 25 | Silk 50 Spider 50 | Cationic dye 1 | 40.2 | 245.2 | 224.1 | 7.8 | 7.8 | 9.4 | Dark blue with metallic luster |
| Example 26 | Spider 100 | Cationic dye 1 | 37.0 | 259.4 | 203.5 | 6.2 | 15.6 | 26.7 | Dark blue with luster |

As shown in Table 6, the physical properties such as stress and toughness of the solution-dyed fiber of Example 25 were low. A phenomenon in which the spinning solution to which the cationic dye was added increased its viscosity was observed. The color tone of the obtained solution-dyed fibers was favorable.

Examples 27-29

In Examples 27-29, a fiber disperse dye was used to prepare solution-dyed fibers. The experiment was performed in the same manner as in Examples 1-5 except that Disperse Black FD (distributed by Shinko Co., Ltd.), which is a disperse dye, was added as a colorant so that the production concentration would be 1 mass %. The obtained solution-dyed fibers (drawn yarns) had the following physical properties.

TABLE 7

| Experiment No. | Ratio of silk:spider (mass %) | Addition amount of dye (mass %) | Single fiber diameter (μm) | Max. stress (MPa) | Average stress (MPa) | Elastic modulus (GPa) | Strain (%) | Toughness (MJ/m$^3$) | Color tone (naked-eye observation) |
|---|---|---|---|---|---|---|---|---|---|
| Example 27 | Silk 100 | Disperse dye 1 | 36.0 | 394.0 | 374.9 | 10.0 | 7.9 | 19.8 | Black |
| Example 28 | Silk 50 Spider 50 | Disperse dye 1 | 41.4 | 210.6 | 195.5 | 6.9 | 8.7 | 13.3 | Black |
| Example 29 | Spider 100 | Disperse dye 1 | 45.4 | 164.6 | 152.6 | 4.8 | 22.2 | 28.9 | Black |

As shown in Table 7, the physical properties such as stress and toughness of the solution-dyed fibers of Examples 27-29 were low as compared with the case of using other dyes. Further, the fiber of spider silk 100% caused more drop of dye in the MeOH coagulation bath than the fibers containing silk.

Examples 30-35, Comparative Example 4

In Examples 30-35 and Comparative Example 4, the spider silk protein described in Example 1 was used, a mixed solvent obtained by adding 8 wt % of LiCL to DMSO was used as a solvent, and the concentration of the spider silk protein was set to 15 wt %. However, in Example 31, the concentration of the spider silk protein was set to 8 wt % to avoid solation. The conditions of the dissolution were a temperature of 90° C. for 3 hours and retention at 80° C. for 12 hours. Each of the dyes or pigments was dissolved or dispersed in DMSO, and added to the dope solution. The concentration of the spider silk protein also includes the content of DMSO in which each of the dyes or pigments was dissolved or dispersed. The viscosities of the dope solutions were as shown in Table 8 below.

TABLE 8

| Experiment No. | Dye | Viscosity at 70° C. (cP) | Viscosity at 80° C. (cP) |
|---|---|---|---|
| Comparative Example 4 | None | 2020 | 1410 |
| Example 30 | Acid dye (0.5 wt %) Acid Milliing Sky Blue FSE | 1877 | 1330 |
| Example 31 | Fluorescent dye (0.5 wt %) NKP-8315 | 1770 | 2017 |
| Example 32 | Natural pigment (0.5 wt %) Safflower Y1500 | 1550 | 1060 |
| Example 33 | Red food dye (0.5 wt %) Red food color No. 102 | 2137 | 1483 |

TABLE 8-continued

| Experiment No. | Dye | Viscosity at 70° C. (cP) | Viscosity at 80° C. (cP) |
|---|---|---|---|
| Example 34 | Carbon black (0.5 wt %) General pigment for fiber solution-dyeing | 3110 | 2133 |
| Example 35 | Disperse dye (0.5 wt %) Disperse Black FD | 7213 | 4773 |

Wet spinning shown in FIG. 3 was performed using the above dope solutions. However, in Example 31, dry-wet spinning was performed. The dry-wet spinning said herein refers to a spinning method in which the distance of the air gap 13 in FIG. 3 is 8 mm. The air gap of the wet spinning is a few millimeters. The dope solution was set at a temperature of 70° C., and extruded into a methanol coagulation liquid at 15° C. Next, an undrawn yarn obtained was subjected to water-bath drawing in water at 50° C., and thereafter drawn at 180° C. using a dry drawing device shown in FIG. 2B. Table 9 shows the conditions, and Table 10 shows the results.

TABLE 9

| Experiment No. | Spinning method | Supply speed (ml/h) | Dry draft (times) | Water-bath draw ratio (times) | Dry-heat draw ratio (times) | Total draw ratio (times) |
|---|---|---|---|---|---|---|
| Comparative Example 4 | Wet spinning | 3 | 1.5 | 2.0 | 1.5 | 4.5 |
| Example 30 | Wet spinning | 3 | 1.5 | 2.0 | 1.5 | 4.5 |
| Example 31 | Dry-wet spinning | 3 | 1.5 | 2.0 | 1.6 | 4.8 |
| Example 32 | Wet spinning | 3 | 1.5 | 2.0 | 1.4 | 4.2 |
| Example 33 | Wet spinning | 3 | 1.5 | 2.0 | 1.5 | 4.5 |
| Example 34 | Wet spinning | 3 | 1.5 | 2.0 | 1.5 | 4.5 |
| Example 35 | Wet spinning | 3.8 | 1.5 | 2.0 | 1.5 | 4.5 |

TABLE 10

| Experiment No. | Average fiber diameter (μm) | Average fineness (decitex) | Max. stress (MPa) | Average stress (MPa) | Strain (%) | Elastic modulus (GPa) | Toughness (MJ/m$^3$) |
|---|---|---|---|---|---|---|---|
| Comparative Example 4 | 43.3 | 29.7 | 280.9 | 222.7 | 5.0 | 9.5 | 8.4 |
| Example 30 | 45.3 | 23.4 | 210.1 | 187.4 | 6.2 | 7.4 | 8.5 |
| Example 31 | 34.3 | 16.9 | 288.0 | 260.1 | 11.0 | 8.9 | 23.2 |
| Example 32 | 56.7 | 25.1 | 125.1 | 121.6 | 7.2 | 4.6 | 6.3 |
| Example 33 | 53.3 | 34.1 | 197.2 | 172.1 | 9.1 | 6.2 | 12.3 |
| Example 34 | 49.7 | 22.6 | 225.4 | 216.1 | 14.2 | 6.4 | 25.2 |
| Example 35 | 53.3 | 31.8 | 332.7 | 295.0 | 15.0 | 8.3 | 36.8 |

The results of the visual inspection of the obtained solution-dyed fiber filament yarns were as follows.

(1) The solution-dyed fiber filament yarn of Example 30 was bright blue with metallic luster.

(2) The solution-dyed fiber filament yarn of Example 31 was bright yellow, and its fluorescence was confirmed using black light.

(3) The solution-dyed fiber filament yarn of Example 32 was bright yellow with metallic luster.

(4) The solution-dyed fiber filament yarn of Example 33 was bright red with metallic luster.

(5) The solution-dyed fiber filament yarn of Example 34 was jet black.

(6) The solution-dyed fiber filament yarn of Example 35 was black with metallic luster In Example 33, the remaining amount of the solvent was measured using a nuclear magnetic resonator (NMR). Since no solvent peak was observed, it is considered that substantially no solvent remained in the solution-dyed fiber filament yarn. Therefore, the solution-dyed fiber was found to be excellent for application to a human body.

INDUSTRIAL APPLICABILITY

Since the protein fiber of the present invention can exhibit bright and beautiful color tone, it can be applied to a fashion product, an ornament, an embroidery thread, a mark such as trademark and a tag, and further to a fishing line, strings of tennis and badminton rackets, a string of a violin, a bowstring of a violin, and artificial hair. It can be in a form of a yarn, a cotton, a weave, a knit, a braid, a nonwoven fabric, etc.

DESCRIPTION OF REFERENCE NUMERALS 1 extrusion process
2, 20 undrawn-yarn production process
3, 30 dry-heat drawing process
4, 26, 32 yarn roll
6, 22 spinning solution
7 storage tank
8 gear pump
9 spinneret
10 spinning-drawing device
11, 25 coagulation liquid
12, 24 coagulation liquid tank
13 air gap
14a-14f yarn guide
15, 27 supply nip roller
16, 28 take-up nip roller
17, 29 dry-heat drawing device
18, 31 guide
21 syringe
33a undrawn yarn
33b drawn yarn
34 water-bath tank
35 water bath
36, 37 nip roller
38 yarn roll
39 water-bath drawing process
40 one cocoon filament
41 two fibroins
42 sericin
43 fibril
44 one cocoon filament Sequence Listing Free Text
SEQ ID NOS: 1-4 amino acid sequence
SEQ ID NOS: 5-7 base sequence
SEQ ID NOS: 8-11 primer sequence

---

The invention claimed is:

1. A solution-dyed protein fiber comprising:
a protein fiber comprising at least one material selected from the group consisting of silk fibroin and a polypeptide derived from spider silk proteins; and
a solution-dyeing colorant,
wherein an amount of the silk fibroin in the protein fiber is in a range of 0-100 mass %, and an amount of the polypeptide derived from spider silk proteins therein is in a range of 100-0 mass %, when an amount of the protein fiber is 100 mass %,
the solution-dyeing colorant is dissolved or dispersed in a spinning solution, of which the solution-dyed protein fiber is formed,
the spinning solution further comprises dimethyl sulfoxide, or N,N-dimethylformamide, or a combination thereof, and
at least one material selected from the group consisting of dimethyl sulfoxide and N,N-dimethylformamide is present in the solution-dyed protein fiber.

2. The solution-dyed protein fiber according to claim 1, wherein the solution-dyeing colorant is at least one material selected from the group consisting of dyes and pigments.

3. The solution-dyed protein fiber according to claim 1, wherein the solution-dyeing colorant is at least one material selected from the group consisting of an acid dye, a basic dye, a fluorescent dye, a direct dye, a disperse dye, a plant pigment, a food natural pigment, and a carbon black.

4. The solution-dyed protein fiber according to claim 1, wherein an amount of the solution-dyeing colorant in the solution-dyed protein fiber is in a range from 0.1 to 2 mass % relative to the protein fiber as 100 mass %.

5. The solution-dyed protein fiber according to claim 1, wherein the solution-dyed protein fiber has a diameter in a range from 5 to 200 μm.

6. The solution-dyed protein fiber according to claim 1, wherein the solution-dyed protein fiber further comprises at least one inorganic salt selected from the group consisting of alkali metal halides, alkaline-earth metal halides, alkaline-earth metal nitrate, and sodium thiocyanate.

7. A method for producing a solution-dyed protein fiber, wherein the solution-dyed protein fiber comprises:
a protein fiber comprising at least one material selected from the group consisting of silk fibroin and a polypeptide derived from spider silk proteins; and
a solution-dyeing colorant,
wherein an amount of the silk fibroin in the protein fiber is in a range of 0-100 mass %, and an amount of the polypeptide derived from spider silk proteins therein is in a range of 100-0 mass %, when an amount of the protein fiber is 100 mass %, and
at least one material selected from the group consisting of dimethyl sulfoxide and N, N-dimethylformamide is present in the solution-dyed protein fiber, and
the method comprises:
dissolving or dispersing the solution-dyeing colorant in a spinning solution, of which the solution-dyed protein fiber is formed, and which further comprises at least one solution selected from the group consisting of dimethyl sulfoxide and N,N-dimethylformamide, thereby forming a coloring liquid;
adding a solvent to the coloring liquid in an amount necessary for a spinning solution;
adding and dissolving protein powder that is capable of forming the protein fiber into the solvent, thereby forming the spinning solution; and
subjecting the spinning solution to wet spinning or dry-wet spinning.

8. The method for producing a solution-dyed protein fiber according to claim 7,
wherein an undrawn yarn of the solution-dyed protein fiber after the wet spinning is heat drawn under dry heat.

9. The method for producing a solution-dyed protein fiber according to claim 8,
wherein the dry-heat drawing is performed at a temperature of 160° C. or higher and at a draw ratio in a range from 1.05 to 4 times.

10. The method for producing a solution-dyed protein fiber according to claim 8,
wherein, before the dry-heat drawing, the undrawn yarn is drawn in water bath in advance.

11. The method for producing a solution-dyed protein fiber according to claim 10,
wherein the water-bath drawing is performed at a temperature in a range from 30° C. to 90° C. and at a draw ratio in a range from 1.05 to 6 times.

12. The method for producing a solution-dyed protein fiber according to claim 7,
wherein the solution-dyeing colorant is at least one material selected from the group consisting of dyes and pigments.

13. The method for producing a solution-dyed protein fiber according to claim 7,
wherein the solution-dyeing colorant is at least one material selected from the group consisting of an acid dye, a basic dye, a fluorescent dye, a direct dye, a disperse dye, a plant pigment, a food natural pigment, and a carbon black.

14. The method for producing a solution-dyed protein fiber according to claim 7, wherein the solution-dyeing colorant is added in an amount in a range from 0.1 to 2 mass % relative to the protein fiber as 100 mass %.

15. The method for producing a solution-dyed protein fiber according to claim 7,
wherein, as the solvent that dissolves the protein powder, the spinning solution includes a solution comprising dimethyl sulfoxide and at least one inorganic salt selected from the group consisting of alkali metal halides, alkaline-earth metal halides, alkaline-earth metal nitrate, and sodium thiocyanate.

* * * * *

SEQUENCE LISTING

<160> NUMBER OF SEQ ID NOS: 11

<210> SEQ ID NO 1
<211> LENGTH: 1154
<212> TYPE: PRT
<213> ORGANISM: Artificial
<220> FEATURE:
<223> OTHER INFORMATION: ADF3Kai-Large-NRSH1

<400> SEQUENCE: 1

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr

-continued

```
            50                  55                  60
Gly Pro Gly Ser Gly Gln Gly Pro Ser Gln Gly Pro Gly Gln
 65                  70                  75                  80
Gln Gly Pro Gly Gly Gln Gly Pro Tyr Gly Pro Gly Ala Ser Ala Ala
                     85                  90                  95
Ala Ala Ala Ala Gly Gly Tyr Gly Pro Gly Ser Gly Gln Gln Gly Pro
                100                 105                 110
Gly Gly Gln Gly Pro Tyr Gly Pro Gly Ser Ser Ala Ala Ala Ala
                115                 120                 125
Ala Gly Gly Asn Gly Pro Gly Ser Gly Gln Gln Gly Ala Gly Gln Gln
            130                 135                 140
Gly Pro Gly Gln Gln Gly Pro Gly Ala Ser Ala Ala Ala Ala Ala
145                 150                 155                 160
Gly Gly Tyr Gly Pro Gly Ser Gly Gln Gln Gly Pro Gly Gln Gln Gly
                165                 170                 175
Pro Gly Gly Gln Gly Pro Tyr Gly Pro Gly Ala Ser Ala Ala Ala Ala
                180                 185                 190
Ala Ala Gly Gly Tyr Gly Pro Gly Ser Gly Gln Gly Pro Gly Gln Gln
            195                 200                 205
Gly Pro Gly Gly Gln Gly Pro Tyr Gly Pro Gly Ala Ser Ala Ala Ala
            210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gly Pro Tyr Gly
                245                 250                 255
Pro Gly Ala Ser Ala Ala Ala Ala Ala Ala Gly Gly Tyr Gly Pro Gly
                260                 265                 270
Tyr Gly Gln Gln Gly Pro Gly Gln Gln Gly Pro Gly Gln Gly Pro
                275                 280                 285
Tyr Gly Pro Gly Ala Ser Ala Ala Ser Ala Ala Ser Gly Gly Tyr Gly
                290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
                325                 330                 335
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gln Gln Gly Pro Tyr Gly
            355                 360                 365
Pro Gly Ala Ser Ala Ala Ala Ala Ala Gly Gly Tyr Gly Pro Gly
            370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
                420                 425                 430
Gln Gly Ala Tyr Gly Pro Gly Ala Ser Ala Ala Gly Ala Ala Gly
            435                 440                 445
Gly Tyr Gly Pro Gly Ser Gly Gln Gly Pro Gly Gln Gln Gly Pro
            450                 455                 460
Gly Gln Gln Gly Pro Gly Gln Gln Gly Pro Gly Gln Gln Gly Pro Gly
465                 470                 475                 480
```

```
Gln Gln Gly Pro Gly Gln Gly Pro Gly Gln Gly Pro Tyr Gly
            485                 490             495

Pro Gly Ala Ser Ala Ala Ala Ala Ala Gly Gly Tyr Gly Pro Gly
            500                 505             510

Ser Gly Gln Gln Gly Pro Gly Gln Gln Gly Pro Gly Gln Gln Gly Pro
            515                 520             525

Gly Gly Gln Gly Pro Tyr Gly Pro Gly Ala Ala Ser Ala Ala Val Ser
            530                 535             540

Val Ser Arg Ala Arg Ala Gly Ser Gln Gln Gly Pro Gly Gln Gln
545             550             555             560

Gly Pro Gly Gln Gln Gly Pro Gly Gln Gln Gly Pro Tyr Gly Pro Gly
            565                 570             575

Ala Ser Ala Ala Ala Ala Ala Ala Gly Gly Tyr Gly Pro Gly Ser Gly
            580                 585             590

Gln Gln Gly Pro Ser Gln Gly Pro Gly Gln Gln Gly Pro Gly Gly
            595             600             605

Gln Gly Pro Tyr Gly Pro Gly Ala Ser Ala Ala Ala Ala Ala Gly
            610             615             620

Gly Tyr Gly Pro Gly Ser Gly Gln Gln Gly Pro Gly Gln Gly Pro
625             630             635             640

Tyr Gly Pro Gly Ser Ser Ala Ala Ala Ala Ala Gly Gly Asn Gly
                645             650             655

Pro Gly Ser Gly Gln Gln Gly Ala Gly Gln Gln Gly Pro Gly Gln Gln
            660             665             670

Gly Pro Gly Ala Ser Ala Ala Ala Ala Ala Gly Gly Tyr Gly Pro
            675             680             685

Gly Ser Gly Gln Gln Gly Pro Gly Gln Gln Gly Pro Gly Gly Gln Gly
            690             695             700

Pro Tyr Gly Pro Gly Ala Ser Ala Ala Ala Ala Ala Gly Gly Tyr
705             710             715             720

Gly Pro Gly Ser Gly Gln Gly Pro Gly Gln Gln Gly Pro Gly Gln
            725             730             735

Gly Pro Tyr Gly Pro Gly Ala Ser Ala Ala Ala Ala Ala Gly Gly
            740             745             750

Tyr Gly Pro Gly Ser Gly Gln Gln Gly Pro Gly Gln Gln Gly Pro Gly
            755             760             765

Gln Gln Gly Pro Gly Gly Gln Gly Pro Tyr Gly Pro Gly Ala Ser Ala
            770             775             780

Ala Ala Ala Ala Gly Gly Tyr Gly Pro Gly Tyr Gly Gln Gln Gly
785             790             795             800

Pro Gly Gln Gln Gly Pro Gly Gln Gly Pro Tyr Gly Pro Gly Ala
            805             810             815

Ser Ala Ala Ser Ala Ala Ser Gly Gly Tyr Gly Pro Gly Ser Gly Gln
            820             825             830

Gln Gly Pro Gly Gln Gln Gly Pro Gly Gln Gln Gly Pro Tyr Gly Pro
            835             840             845

Gly Ala Ser Ala Ala Ala Ala Ala Gly Gly Tyr Gly Pro Gly Ser
850             855             860

Gly Gln Gln Gly Pro Gly Gln Gln Gly Pro Gly Gln Gln Gly Pro Gly
865             870             875             880

Gln Gln Gly Pro Gly Gly Gln Gly Pro Tyr Gly Pro Gly Ala Ser Ala
            885             890             895
```

Ala Ala Ala Ala Ala Gly Gly Tyr Gly Pro Gly Ser Gly Gln Gln Gly
                900                 905                 910

Pro Gly Gln Gln Gly Pro Gly Gln Gln Gly Pro Gly Gln Gln Gly Pro
            915                 920                 925

Gly Gln Gln Gly Pro Gly Gln Gln Gly Pro Gly Gln Gln Gly Pro Gly
        930                 935                 940

Gln Gln Gly Pro Gly Gln Gln Gly Pro Gly Gln Gln Gly Ala Tyr Gly
945                 950                 955                 960

Pro Gly Ala Ser Ala Ala Ala Gly Ala Ala Gly Tyr Gly Pro Gly
            965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
        995                 1000                1005

Gln Gln Gly Pro Gly Gln Gln Gly Pro Gly Gln Gln Gly Pro Gly Ala Ser
    1010                1015                1020

Ala Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 2
<211> LENGTH: 660
<212> TYPE: PRT
<213> ORGANISM: Artificial
<220> FEATURE:
<223> OTHER INFORMATION: ADF3Kai

<400> SEQUENCE: 2

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
            85                  90                  95

```
Ala Ala Ala Ala Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gly Gln Gln Gly Ala Gly Gln Gln
            130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
            165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
            210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
            245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
            275                 280                 285

Tyr Gly Pro Gly Ala Ser Ala Ala Ser Ala Ala Ser Gly Gly Tyr Gly
            290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gln Gln Gly Pro Gly Gln Gln Gly Pro Gly
            340                 345                 350

Gln Gln Gly Pro Gly Gln Gln Gly Pro Gly Gln Gln Gly Pro Tyr Gly
            355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
            405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
            435                 440                 445

Gly Tyr Gly Pro Gly Ser Gly Gln Gln Gly Pro Gly Gln Gln Gly Pro
            450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
```

-continued

```
                515                 520                 525
Gly Gly Gln Gly Pro Tyr Gly Pro Gly Ala Ser Ala Ala Val Ser
            530                 535                 540
Val Gly Gly Tyr Gly Pro Gln Ser Ser Val Pro Val Ala Ser Ala
545                 550                 555                 560
Val Ala Ser Arg Leu Ser Ser Pro Ala Ala Ser Ser Arg Val Ser Ser
                565                 570                 575
Ala Val Ser Ser Leu Val Ser Ser Gly Pro Thr Lys His Ala Ala Leu
            580                 585                 590
Ser Asn Thr Ile Ser Ser Val Val Ser Gln Val Ser Ala Ser Asn Pro
                595                 600                 605
Gly Leu Ser Gly Cys Asp Val Leu Val Gln Ala Leu Leu Glu Val Val
            610                 615                 620
Ser Ala Leu Val Ser Ile Leu Gly Ser Ser Ile Gly Gln Ile Asn
625                 630                 635                 640
Tyr Gly Ala Ser Ala Gln Tyr Thr Gln Met Val Gly Gln Ser Val Ala
                645                 650                 655
Gln Ala Leu Ala
            660

<210> SEQ ID NO 3
<211> LENGTH: 1183
<212> TYPE: PRT
<213> ORGANISM: Artificial
<220> FEATURE:
<223> OTHER INFORMATION: ADF3Kai-Large

<400> SEQUENCE: 3

Met His His His His His His His His His Ser Ser Gly Ser Ser
1               5                   10                  15
Leu Glu Val Leu Phe Gln Gly Pro Ala Arg Ala Gly Ser Gly Gln Gln
                20                  25                  30
Gly Pro Gly Gln Gln Gly Pro Gly Gln Gln Gly Pro Gly Gln Gln Gly
            35                  40                  45
Pro Tyr Gly Pro Gly Ala Ser Ala Ala Ala Ala Ala Gly Gly Tyr
50                  55                  60
Gly Pro Gly Ser Gly Gln Gln Gly Pro Ser Gln Gln Gly Pro Gly Gln
65                  70                  75                  80
Gln Gly Pro Gly Gly Gln Gly Pro Tyr Gly Pro Gly Ala Ser Ala Ala
                85                  90                  95
Ala Ala Ala Ala Gly Gly Tyr Gly Pro Gly Ser Gly Gln Gln Gly Pro
            100                 105                 110
Gly Gly Gln Gly Pro Tyr Gly Pro Gly Ser Ala Ala Ala Ala
            115                 120                 125
Ala Gly Gly Asn Gly Pro Gly Ser Gly Gln Gln Gly Ala Gly Gln Gln
            130                 135                 140
Gly Pro Gly Gln Gln Gly Pro Gly Ala Ser Ala Ala Ala Ala Ala
145                 150                 155                 160
Gly Gly Tyr Gly Pro Gly Ser Gly Gln Gln Gly Pro Gly Gln Gln Gly
                165                 170                 175
Pro Gly Gly Gln Gly Pro Tyr Gly Pro Gly Ala Ser Ala Ala Ala Ala
            180                 185                 190
Ala Ala Gly Gly Tyr Gly Pro Gly Ser Gly Gln Gly Pro Gln Gln
            195                 200                 205
Gly Pro Gly Gly Gln Gly Pro Tyr Gly Pro Gly Ala Ser Ala Ala Ala
```

-continued

```
            210                 215                 220
Ala Ala Gly Gly Tyr Gly Pro Gly Ser Gly Gln Gly Pro Gly
225                 230                 235                 240

Gln Gly Pro Gly Gln Gly Pro Gly Gln Gly Pro Tyr Gly
                245                 250                 255

Pro Gly Ala Ser Ala Ala Ala Ala Ala Gly Gly Tyr Gly Pro Gly
                260                 265                 270

Tyr Gly Gln Gln Gly Pro Gly Gln Gln Gly Pro Gly Gln Gly Pro
                275                 280                 285

Tyr Gly Pro Gly Ala Ser Ala Ala Ser Ala Ala Ser Gly Gly Tyr Gly
                290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
                325                 330                 335

Tyr Gly Pro Gly Ser Gly Gln Gln Gly Pro Gly Gln Gln Gly Pro Gly
                340                 345                 350

Gln Gln Gly Pro Gly Gln Gln Gly Pro Gly Gln Gln Gly Pro Tyr Gly
                355                 360                 365

Pro Gly Ala Ser Ala Ala Ala Ala Ala Gly Gly Tyr Gly Pro Gly
370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
                420                 425                 430

Gln Gly Ala Tyr Gly Pro Gly Ala Ser Ala Ala Ala Gly Ala Ala Gly
                435                 440                 445

Gly Tyr Gly Pro Gly Ser Gly Gln Gln Gly Pro Gly Gln Gln Gly Pro
                450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
                500                 505                 510

Ser Gly Gln Gln Gly Pro Gly Gln Gln Gly Pro Gly Gln Gln Gly Pro
                515                 520                 525

Gly Gly Gln Gly Pro Tyr Gly Pro Gly Ala Ala Ser Ala Ala Val Ser
530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Ala Gly Gly Tyr Gly Pro Gly Ser Gly
                580                 585                 590

Gln Gln Gly Pro Ser Gln Gly Pro Gly Gln Gln Gly Pro Gly Gly
                595                 600                 605

Gln Gly Pro Tyr Gly Pro Gly Ala Ser Ala Ala Ala Ala Ala Gly
                610                 615                 620

Gly Tyr Gly Pro Gly Ser Gly Gln Gln Gly Pro Gly Gly Gln Gly Pro
625                 630                 635                 640
```

-continued

Tyr Gly Pro Gly Ser Ser Ala Ala Ala Ala Gly Gly Asn Gly
            645                 650                 655

Pro Gly Ser Gly Gln Gln Gly Ala Gly Gln Gly Pro Gly Gln Gln
            660                 665                 670

Gly Pro Gly Ala Ser Ala Ala Ala Ala Gly Gly Tyr Gly Pro
        675                 680                 685

Gly Ser Gly Gln Gln Gly Pro Gly Gln Gln Gly Pro Gly Gln Gly
        690                 695                 700

Pro Tyr Gly Pro Gly Ala Ser Ala Ala Ala Ala Gly Gly Tyr
705                 710                 715                 720

Gly Pro Gly Ser Gly Gln Gly Pro Gly Gln Gln Gly Pro Gly Gln
            725                 730                 735

Gly Pro Tyr Gly Pro Gly Ala Ser Ala Ala Ala Ala Gly Gly
            740                 745                 750

Tyr Gly Pro Gly Ser Gly Gln Gln Gly Pro Gly Gln Gln Gly Pro Gly
            755                 760                 765

Gln Gln Gly Pro Gly Gly Gln Gly Pro Tyr Gly Pro Gly Ala Ser Ala
770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
            805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gln Gly Pro Tyr Gly Pro
            835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
            885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
            915                 920                 925

Gly Gln Gln Gly Pro Gly Gln Gln Gly Pro Gly Gln Gln Gly Pro Gly
            930                 935                 940

Gln Gln Gly Pro Gly Gln Gln Gly Pro Gly Gln Gln Gly Ala Tyr Gly
945                 950                 955                 960

Pro Gly Ala Ser Ala Ala Ala Gly Ala Ala Gly Gly Tyr Gly Pro Gly
            965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
            995                 1000                1005

Gln Gln Gly Pro Gly Gln Gln Gly Pro Tyr Gly Pro Gly Ala Ser
            1010                1015                1020

Ala Ala Ala Ala Ala Ala Gly Gly Tyr Gly Pro Gly Ser Gly Gln
            1025                1030                1035

Gln Gly Pro Gly Gln Gln Gly Pro Gly Gln Gln Gly Pro Gly Gly
            1040                1045                1050

```
Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu Gly Ser Ser Ser
    1145                1150                1155

Ile Gly Gln Ile Asn Tyr Gly Ala Ser Ala Gln Tyr Thr Gln Met
    1160                1165                1170

Val Gly Gln Ser Val Ala Gln Ala Leu Ala
    1175                1180
```

<210> SEQ ID NO 4
<211> LENGTH: 24
<212> TYPE: PRT
<213> ORGANISM: Artificial
<220> FEATURE:
<223> OTHER INFORMATION: His tag and start codon

<400> SEQUENCE: 4

```
Met His His His His His His His His His Ser Ser Gly Ser Ser
1               5                   10                  15

Leu Glu Val Leu Phe Gln Gly Pro
            20
```

<210> SEQ ID NO 5
<211> LENGTH: 1983
<212> TYPE: DNA
<213> ORGANISM: Artificial
<220> FEATURE:
<223> OTHER INFORMATION: ADF3Kai

<400> SEQUENCE: 5

```
atgcatcacc atcatcatca tcaccaccac cattcctcgg gctcatcctt ggaagtgtta     60
tttcaaggac cagcacgagc cggttcggga acaagggc ctggccagca gggcccaggt      120
caacaagggc caggacagca gggtccttat gggcccggcg caagcgcagc agctgcggcc    180
gctggtggct atggtcctgg ctccggtcaa caggcccctt cgcaacaagg tcccgggcag    240
caaggtcctg gtggccaggg tcctacgggc cggggcga gtgcggcagc agccgctgca      300
ggcggttatg gtccaggaag cggacagcaa ggtccgggag gtcaaggtcc gtatggccca   360
ggctctagcg cggctgccgc tgccgcgggt ggcaacggac agggagcgg acaacagggc    420 gcgggacaac agggtccagg acagcaaggc ccagggcgt cggcggctgc agcggcggcc    480
ggaggctatg acccggctc aggacaacag gaccgggtc aacaaggacc cggtggccaa    540
ggcccctatg gccgggcgc cagcgcggcc gcagccgccg cgggcgggta cggcccggt     600 agcggccagg gaccaggtca gcaggggcca ggaggtcagg gcccatacgg tccgggcgca    660
tccgcggcgg cggcagcggc aggtggctac ggtcccggaa gcggccaaca ggggccaggg    720
caacaaggac caggacaaca aggtcctggg ggccaaggac gtatggacc aggagcatca    780
```

```
gctgcagccg cggcagctgg cggttacggt ccaggctacg ccagcaggg tccgggtcag    840 cagggaccgg gaggccaggg gccttatggc cctggcgctt ccgcagccag tgccgcttct    900
ggaggatacg ggccgggaag cggtcagcaa ggccctggcc aacaaggacc tggaggccaa    960
gggccctacg gcccaggagc ctcggcagcc gcagctgccg caggtgggta tgggccaggt   1020
agcgggcaac aagggccggg tcagcaagga ccggggcaac agggacctgg cagcaagga   1080 cccgggggtc aaggcccgta cggacctggt gcgtctgcag ctgctgctgc ggctggtgga   1140
tatggtccgg gatcggggca gcagggtccc ggtcagcagg gccctggtca gcaagggcca   1200
ggccaacagg gacccggaca caaggcccg ggtcaacagg gtcctggaca gcaggggccg   1260
ggccaacaag gccctgggca cagggtccg ggggacagg gggcctatgg gcctggcgca   1320
tctgccgccg ctggcgcagc cggtgggtac gggcctgggt caggtcaaca ggggcctggt   1380
caacaaggcc ccgggcaaca gggccccggc cagcaaggtc cagggcagca gggcccggga   1440
cagcaagggc ctggacaaca ggggcccgga cagcagggac cttacgggcc cggtgcgagc   1500
gcagcggccg ccgccgcagg gggatatggc cccggatcgg gccagcaggg accaggccag   1560
caaggacctg gccaacaggg cccgggggt cagggggccgt atggtccgg cgctgcaagt   1620 gctgcagtgt ccgttggagg ttacggccct cagtcttcgt ctgttccggt ggcgtccgca   1680
gttgcgagta gactgtcttc acctgctgct tcatcgcgag tatcgagcgc tgtttcgtct   1740
cttgtctcgt cgggtcccac gaaacatgcc gccctttcaa atacgatttc atctgtagtg   1800
tcccaagtta gtgcaagtaa cccggggtta tccggatgcg acgttctcgt tcaggcactc   1860
ctagaagtag tatccgcgtt ggtgagcatc ttaggcagct cctcgatagg tcaaataaac   1920
tatggtgctt cagcccagta tacacagatg gtgggacaga gcgtcgcgca ggcattggct   1980
taa                                                                 1983

<210> SEQ ID NO 6
<211> LENGTH: 3552
<212> TYPE: DNA
<213> ORGANISM: Artificial
<220> FEATURE:
<223> OTHER INFORMATION: ADF3Kai-Large

<400> SEQUENCE: 6
atgcatcacc atcatcatca tcaccaccac cattcctcgg gctcatcctt ggaagtgtta     60
tttcaaggac cagcacgagc cggttcggga caacaagggc ctggccagca gggcccaggt    120
caacaagggc caggacagca gggtccttat gggcccggcg caagcgcagc agctgcggcc    180
gctggtggct atggtcctgg ctccggtcaa cagggcccctt cgcaacaagg tcccgggcag    240
caaggtcctg gtggccaggg tcctacgggg ccggggcga gtgcggcagc agccgctgca    300
ggcggttatg gtccaggaag cggacagcaa ggtccggag gtcaaggtcc gtatggccca    360
ggctctagcg cggctgccgc tgccgcgggt ggcaacggac cagggagcgg acaacagggc    420
gcgggacaac agggtccagg acagcaaggc cagggggcgt cggcggctgc agcggcggcc    480
ggaggctatg gacccggctc aggacaacag ggaccgggtc aacaaggacc cggtggccaa    540
ggcccctatg gccgggcgc cagcgcggcc gcagccgccg cggcggggta cggccccggt    600
agcggccagg gaccaggtca gcaggggcca ggaggtcagg gcccatacgg tccgggcgca    660
tccgcggcgg cggcagcggc agtggcctac ggtcccggaa gcggccaaca ggggccaggg    720
caacaaggac caggacaaca aggtcctggg ggccaaggac gtatggacc aggagcatca    780 gctgcagccg cggcagctgg cggttacggt ccaggctacg ccagcaggg tccgggtcag    840
```

```
cagggaccgg gaggccaggg gccttatggc cctggcgctt ccgcagccag tgccgcttct      900
ggaggatacg ggccgggaag cggtcagcaa ggccctggcc aacaaggacc tggaggccaa      960
gggccctacg gcccaggagc ctcggcagcc gcagctgccg caggtgggta tgggccaggt     1020
agcgggcaac aagggccggg tcagcaagga ccggggcaac agggacctgg gcagcaagga     1080
cccgggggtc aaggcccgta cggacctggt gcgtctgcag ctgctgctgc ggctggtgga     1140
tatggtccgg gatcggggca gcagggtccc ggtcagcagg gccctggtca gcaagggcca     1200
ggccaacagg gacccggaca acaaggcccg ggtcaacagg gtcctggaca gcagggccg      1260 ggccaacaag gccctgggca cagggtccg ggggacaggg gggcctatgg gcctggcgca      1320
tctgccgccg ctggcgcagc cggtgggtac gggcctgggt caggtcaaca ggggcctggt     1380
caacaaggcc ccgggcaaca gggcccggc cagcaaggtc cagggcagca gggcccggga      1440
cagcaagggc ctggacaaca ggggcccgga cagcagggac cttacgggcc cggtgcgagc     1500
gcagcggccg ccgccgcagg gggatatggc cccggatcgg gccagcaggg accaggccag     1560
caaggacctg gccaacaggg cccgggggt cagggggccgt atggtcccgg cgctgcaagt     1620
gctgcagtgt ccgtttctag agcacgagcc ggttcgggac aacaagggcc tggcagcag      1680 ggcccaggtc aacaagggcc aggacagcag gtccttatg ggcccggcgc aagcgcagca      1740
gctgcggccg ctggtggcta tggtcctggc tccggtcaac agggcccttc gcaacaaggt     1800
cccgggcagc aaggtcctgg tggccaggt cctacgggc cgggggcgag tgcggcagca      1860
gccgctgcag gcggttatgg tccaggaagc ggacagcaag gtccgggagg tcaaggtccg     1920
tatggcccag gctctagcgc ggctgccgct ccgcgggtg gcaacggacc agggagcgga     1980
caacagggcg cggacaaca gggtccagga cagcaaggcc caggggcgtc ggcggctgca     2040
gcggcggccg gaggctatgg acccggctca ggacaacagg gaccgggtca acaaggaccc     2100
ggtggccaag gccctatgg ccgggcgcc agcgcggccg cagccgcgc gggcgggtac       2160 ggccccggta gcgccaggg accaggtcag caggggccag gaggtcaggg cccatacggt     2220 ccggggcgcat ccgcgcggc ggcagcgca gtggcgtacg gtcccggaag cggccaacag     2280
gggccagggc aacaaggacc aggacaacaa ggtcctgggg gccaaggacc gtatggacca     2340
ggagcatcag ctgcagccgc ggcagctggc ggttacggtc caggctacgg ccagcagggt     2400 ccgggtcag agggaccggg aggccaggg ccttatggcc ctggcgcttc cgcagccagt     2460
gccgcttctg gaggatacgg gccgggaagc ggtcagcaag gccctggcca acaaggacct     2520
ggaggccaag ggccctacgg cccaggagcc tcggcagccg cagctgccgc aggtggatt     2580 ggccaggta gcgggcaaca agggccgggt cagcaaggac cgggcaaca gggacctggg     2640 cagcaaggac ccgggggtca aggcccgtac ggacctggtg cgtctgcagc tgctgctgcg     2700
gctggtggat atggtccggg atcggggcag cagggtcccg gtcagcaggg ccctggtcag     2760
caagggccag ccaacaggg acccggacaa caaggcccgg gtcaacaggg tcctggacag     2820 cagggccgg gccaacaagg ccctgggcaa cagggtccgg ggggacaggg ggcctatggg     2880
cctggcgcat ctgccgccgc tggcgcagcc ggtgggtacg ggcctgggtc aggtcaacag     2940
gggcctggtc aacaaggccc cgggcaacag ggccccggcc agcaaggtcc agggcagcag     3000
ggcccgggac agcaagggcc tggacaacag gggcccggac agcaggggacc ttacgggccc     3060 ggtgcgagcg cagcggccgc cgccgcaggg ggatatggcc ccggatcggg ccagcaggga     3120
ccaggccagc aaggacctgg ccaacagggc ccgggggtc agggggccgta tggtcccggc     3180
```

```
gctgcaagtg ctgcagtgtc cgttggaggt tacggccctc agtcttcgtc tgttccggtg    3240
gcgtccgcag ttgcgagtag actgtcttca cctgctgctt catcgcgagt atcgagcgct    3300
gtttcgtctc ttgtctcgtc gggtcccacg aaacatgccg cccttcaaa tacgatttca     3360 tctgtagtgt cccaagttag tgcaagtaac ccggggttat ccggatgcga cgttctcgtt    3420
caggcactcc tagaagtagt atccgcgttg gtgagcatct taggcagctc ctcgataggt    3480
caaataaact atggtgcttc agcccagtat acacagatgg tgggacagag cgtcgcgcag    3540
gcattggctt aa                                                        3552
```

<210> SEQ ID NO 7
<211> LENGTH: 3465
<212> TYPE: DNA
<213> ORGANISM: Artificial
<220> FEATURE:
<223> OTHER INFORMATION: ADF3Kai-Large-NRSH1

<400> SEQUENCE: 7

```
atgcatcacc atcatcatca tcaccaccac cattcctcgg gctcatcctt ggaagtgtta     60
tttcaaggac cagcacgagc cggttcggga caacaagggc ctggccagca gggcccaggt    120
caacaagggc caggacagca gggtccttat gggcccggcg caagcgcagc agctgcggcc    180
gctggtggct atggtcctgg ctccggtcaa cagggccctt cgcaacaagg tcccgggcag    240
caaggtcctg gtgccaggg tcctacgggc cggggggcga gtgcggcagc agccgctgca     300
ggcggttatg gtccaggaag cggacagcaa ggtccgggag gtcaaggtcc gtatggccca    360
ggctctagcg cggctgccgc tgccgcgggt ggcaacggac cagggagcgg acaacagggc    420
gcgggacaac agggtccagg acagcaaggc ccaggggcgt cggcggctgc agcggcggcc    480
ggaggctatg gacccggctc aggacaacag ggaccgggtc aacaaggacc cggtggccaa    540
ggcccctatg gcccgggcgc cagcgcggcc gcagccgccg cgggcgggta cggccccggt    600
agcggccagg gaccaggtca gcaggggcca ggaggtcagg gcccatacgg tccgggcgca    660
tccgcggcgg cggcagcggc aggtggctac ggtccggaa gcggccaaca ggggccaggg    720
caacaaggac caggacaaca aggtcctggg ggccaaggac cgtatggacc aggagcatca    780
gctgcagccg cggcagctgg cggttacggt ccaggctacg ccagcaggg tccgggtcag    840 cagggaccgg gaggccaggg gccttatggc cctggcgctt ccgcagccag tgccgcttct    900
ggaggatacg ggccgggaag cggtcagcaa ggccctggcc aacaaggacc tggaggccaa    960
gggccctacg gccaggagc ctcggcagcc gcagctgccg caggtgggta tgggccaggt   1020
agcgggcaac aagggccggg tcagcaagga ccggggcaac agggacctgg gcagcaagga   1080
cccgggggtc aaggcccgta cggacctggt gcgtctgcag ctgctgctgc ggctggtgga   1140
tatggtccgg gatcggggca gcagggtccc ggtcagcagg ccctggtca gcaagggcca   1200 ggccaacagg gacccggaca acaaggcccg gtcaacagg gtcctggaca gcaggggccg   1260
ggccaacaag gccctgggca cagggtccg gggacagg gggcctatgg gcctggcgca    1320
tctgccgccg ctggcgcagc cggtgggtac gggcctgggt caggtcaaca ggggcctggt   1380
caacaaggcc ccgggcaaca gggccccggc cagcaaggtc cagggcagca gggcccggga   1440
cagcaagggc ctggacaaca ggggcccgga cagcagggac cttacgggcc cggtgcgagc   1500
gcagcggccg ccgccgcagg gggatatggc cccggatcgg gccagcaggg accaggccag   1560
caaggacctg ccaacaggg cccgggggt caggggccgt atggtccgg cgctgcaagt    1620 gctgcagtgt ccgtttctag agcacgagcc ggttcgggac aacaagggcc tggccagcag   1680
```

```
ggcccaggtc aacaagggcc aggacagcag ggtccttatg ggcccggcgc aagcgcagca    1740
gctgcggccg ctggtggcta tggtcctggc tccggtcaac agggcccttc gcaacaaggt    1800
cccgggcagc aaggtcctgg tggccagggt ccctacgggc cggggcgag tgcggcagca     1860 gccgctgcag gcggttatgg tccaggaagc ggacagcaag gtccgggagg tcaaggtccg    1920
tatggcccag gctctagcgc ggctgccgct gccgcgggtg caacggacc agggagcgga     1980 caacagggcg cgggacaaca gggtccagga cagcaaggcc caggggcgtc ggcggctgca    2040
gcggcggccg gaggctatgg acccggctca ggacaacagg gaccgggtca acaaggaccc    2100
ggtggccaag gccctatgg cccgggcgcc agcgcgccg cagccgccgc gggcgggtac      2160
ggccccggta gcggccaggg accaggtcag caggggccag gaggtcaggg cccatacggt    2220
ccgggcgcat ccgcggcggc ggcagcggca gtggctacg gtcccggaag cggccaacag     2280
gggccagggc aacaaggacc aggacaacaa ggtcctgggg gccaaggacc gtatggacca    2340
ggagcatcag ctgcagccgc ggcagctggc ggttacggtc caggctacgg ccagcagggt    2400
ccgggtcagc agggaccggg aggccagggg ccttatggcc ctggcgcttc cgcagccagt    2460
gccgcttctg gaggatacgg gccgggaagc ggtcagcaag gccctggcca acaaggacct    2520
ggaggccaag ggccctacgg cccaggagcc tcggcagccg cagctgccgc aggtgggtat    2580
gggccaggta gcgggcaaca agggccgggt cagcaaggac cggggcaaca gggacctggg    2640
cagcaaggac ccgggggtca aggcccgtac ggacctggtg cgtctgcagc tgctgctgcg    2700
gctggtggat atggtccggg atcgggcag caggtcccg gtcagcaggg ccctggtcag     2760
caagggccag gccaacaggg acccggacaa caaggcccgg gtcaacaggg tcctggacag    2820
caggggccgg gccaacaagg ccctgggcaa caggtccgg ggacagggg ggcctatggg      2880 cctggcgcat ctgccgccgc tggcgcagcc ggtgggtacg ggcctgggtc aggtcaacag    2940
gggcctggtc aacaaggccc cgggcaacag ggccccggcc agcaaggtcc agggcagcag    3000
ggcccgggac agcaagggcc tggacaacag gggcccggac agcaggacc ttacgggccc     3060 ggtgcgagcg cagcggccgc cgccgcaggg ggatatggcc ccggatcggg ccagcaggga    3120
ccaggccagc aaggacctgg ccaacagggc cgggggggtc aggggccgta tggtcccggc    3180
gctgcaagtg ctgcagtgtc cgttggaggt tacggccctc agtcttcgtc tgttccggtg    3240
gcgtccgcag ttgcgagtag actgtcttca cctgctgctt catcgcgagt atcgagcgct    3300
gtttcgtctc ttgtctcgtc gggtcccacg aaacatgccg ccctttcaaa tacgatttca    3360
tctgtagtgt cccaagttag tgcaagtaac ccggggttat ccggatgcga cgttctcgtt    3420
caggcactcc tagaagtagt atccgcgttg gtgagcatct tataa                   3465
```

<210> SEQ ID NO 8
<211> LENGTH: 20
<212> TYPE: DNA
<213> ORGANISM: Artificial
<220> FEATURE:
<223> OTHER INFORMATION: T7 promoter primer

<400> SEQUENCE: 8
taatacgact cactataggg                                                  20

<210> SEQ ID NO 9
<211> LENGTH: 27
<212> TYPE: DNA
<213> ORGANISM: Artificial
<220> FEATURE:

```
<223> OTHER INFORMATION: Rep Xba I primer

<400> SEQUENCE: 9
tctagaaacg gacactgcag cacttgc                                    27

<210> SEQ ID NO 10
<211> LENGTH: 28
<212> TYPE: DNA
<213> ORGANISM: Artificial
<220> FEATURE:
<223> OTHER INFORMATION: Xba I Rep primer

<400> SEQUENCE: 10
tctagagcac gagccggttc gggacaac                                   28

<210> SEQ ID NO 11
<211> LENGTH: 19
<212> TYPE: DNA
<213> ORGANISM: Artificial
<220> FEATURE:
<223> OTHER INFORMATION: T7 terminator primer

<400> SEQUENCE: 11
gctagttatt gctcagcgg                                             19
```